US008435790B2

(12) United States Patent
Farese, Jr. et al.

(10) Patent No.: US 8,435,790 B2
(45) Date of Patent: May 7, 2013

(54) METHODS OF MODULATING LIPID CONCENTRATIONS IN EUKARYOTIC CELLS

(75) Inventors: Robert V. Farese, Jr., San Francisco, CA (US); Yi Guo, Orinda, CA (US); Tobias C. Walther, Munich (DE); Peter Walter, San Francisco, CA (US)

(73) Assignees: The Regents of the University of California, Oakland, CA (US); The J. David Gladstone Institutes, San Francisco, CA (US)

(*) Notice: Subject to any disclaimer, the term of this patent is extended or adjusted under 35 U.S.C. 154(b) by 515 days.

(21) Appl. No.: 12/508,853

(22) Filed: Jul. 24, 2009

(65) Prior Publication Data
US 2010/0021912 A1  Jan. 28, 2010

Related U.S. Application Data

(60) Provisional application No. 61/083,697, filed on Jul. 25, 2008.

(51) Int. Cl.
C12N 15/01 (2006.01)
(52) U.S. Cl.
USPC ............ 435/441; 435/446; 435/455; 435/470
(58) Field of Classification Search .................. None
See application file for complete search history.

(56) References Cited

U.S. PATENT DOCUMENTS

| | | | |
|---|---|---|---|
| 4,324,067 | A | 4/1982 | Kessler |
| 5,279,833 | A | 1/1994 | Rose |
| 5,389,069 | A | 2/1995 | Weaver |
| 5,516,923 | A | 5/1996 | Hebert et al. |
| 5,578,090 | A | 11/1996 | Bradin |
| 5,908,779 | A | 6/1999 | Carmichael et al. |
| 5,928,944 | A | 7/1999 | Seth et al. |
| 6,015,440 | A | 1/2000 | Noureddini |
| 6,027,900 | A | 2/2000 | Allnutt et al. |
| 7,135,308 | B1 | 11/2006 | Bush et al. |
| 7,294,504 | B1 | 11/2007 | Wang |
| 2004/0006792 | A1 | 1/2004 | Fillatti et al. |
| 2004/0043389 | A1 | 3/2004 | McCarthy |
| 2004/0074760 | A1 | 4/2004 | Portnoff et al. |
| 2005/0034190 | A9 | 2/2005 | Fillatti et al. |
| 2005/0053591 | A1* | 3/2005 | Pun .............................. 424/94.1 |
| 2006/0174380 | A1 | 8/2006 | Carrington et al. |
| 2007/0025969 | A1 | 2/2007 | Roelvink et al. |
| 2007/0048848 | A1 | 3/2007 | Sears |
| 2007/0214516 | A1 | 9/2007 | Fillatti et al. |

FOREIGN PATENT DOCUMENTS
EP         0108580 A1   10/1983

OTHER PUBLICATIONS

Guo et al., The Journal of Cell Biology, vol. 125, No. 6, Jun. 1994, pp. 1213-1224.*
Dascher et al., The Journal of Biological Chemistry, vol. 269, No. 2, 1994, pp. 1437-1448.*
Teal et al., The Journal of Biological Chemistry, vol. 269, No. 5, Feb. 4, 1994, pp. 3135-3138.*
Park et al., Molecular Biology of the Cell, vol. 16, 2005, pp. 3786-3799.*
Leslie R. Ballou, et al., "Interleukin-1-mediated PGE2 Production and Sphingomyelin," J. Biol. Chem., Oct. 5, 1992, vol. 267, No. 28, 20044-20050.
Takeshi Itoh, et al.,"Curated genome annotation of *Oryza sativa* ssp. japonica and comparative genome analysis with *Arabidopsis thaliana*," Genome Research, 2007, 17:175-183.
William R. Pearson, et al., "Improved tools for biological sequence comaprison," Proc. Natl. Acad. Sci. USA, Apr. 1988, vol. 85, 2444-2448.
Mathia Beller, et al., "COPI Complex Is a Regulator of Lipid Homeostasis," PLoS Biology, Nov. 2008, vol. 6, No. 11, 2530-2549.
Yi Guo, et al., "Lipid droplets at a glance," J. of Cell Science, 2009, 122, 749-752, doi:10.1242/jcs.037630.
Dawn L. Brasaemle, et al., Proteomic Analysis of Proteins Associated with Lipid Droplets of Basal and Lipolytically Stimulated 3T3-L1 Adipocytes, The Journal of Biological Chemistry, vol. 279, No. 45, Issue of Nov. 5, pp. 46835-46842, 2004.
Scott E Franklin, et al., "Prospects for molecular farming in the green alga *Chlamydomonas reinhardtii*", Plant Biotechnology, Current Opinion in Plant Biology 2004, 7:159-165.
Rafael Garcia-Mata, et al., "ARF/COPI-dependent events at the ER-Golgi interface are regulated by the guanine-nucleotide exchange factor GBF1", Department of Cell Biology, University of Alabama at Birmingham, Apr. 4, 2003, pp. 1-45.
Vyacheslav Andrianov, et al., "Tobacco as a Production Platform for Biofuel: Overexpression of *Arabidopsis* DGAT and LEC2 Genes Increases Accumulation and Shifts the Composition of Lipids in Green Biomass" Plant Biotech Journal (2010) 8, pp. 277-287.
Yi Guo, et al., "Functional genomic screen reveals genes involved in lipid-droplet formation and utilization," Nature, May 2008, doi:10.1038/nature06928.
Kouhei Takashima, et al., "GBF1-Arf-COPI-ArfGAP-mediated Golgi-to-ER Transport Involved in Regulation of Lipid Homeostatis," Cell Structure and Function, 2011, 36:223-235.
Krishnakant G. Soni, et al., "Coatomer-dependent protein delivery to lipid droplets," Journal of Cell Science, 2009, 122:1834-1841.

* cited by examiner

*Primary Examiner* — Jim Ketter
(74) *Attorney, Agent, or Firm* — David J. Aston; Peters Verny, LLP

(57) ABSTRACT

The present invention is based on the discovery of a set of genes that are involved in lipid-droplet formation and regulation. Accordingly, the present invention provides methods of increasing or decreasing lipid concentrations in eukaryotic cells by decreasing or increasing expression of one of these genes. Increased lipid concentrations may be useful, for example, in the generation of biofuels. Decreased lipid concentration may be useful in the treatment of diseases characterized by excessive lipid storage. In addition, the invention provides methods of identifying markers of diseases characterized by excessive lipid storage.

9 Claims, 10 Drawing Sheets

METHODS OF MODULATING LIPID CONCENTRATIONS IN EUKARYOTIC CELLS

CROSS-REFERENCE TO RELATED APPLICATIONS

This application claims priority from U.S. Provisional Patent Application No. 61/083,697 filed on Jul. 25, 2008, which is hereby incorporated by reference.

STATEMENT OF GOVERNMENTAL SUPPORT

This invention was made with government support under Grant Number DK078254-01 awarded by the National Institutes of Health. The government has certain rights in this invention.

REFERENCE TO SEQUENCE LISTING, COMPUTER PROGRAM, OR COMPACT DISK

Applicants assert that the text copy of the Sequence Listing is identical to the Sequence Listing in computer readable form found on the accompanying computer file. Applicants hereby incorporate the contents of the sequence listing by reference in its entirety.

BACKGROUND OF THE INVENTION

1. Field of the Invention

The present invention relates to the field of lipid-droplet cell biology.

2. Related Art

Presented below is background information on certain aspects of the present invention as they may relate to technical features referred to in the detailed description, but not necessarily described in detail. The discussion below should not be construed as an admission as to the relevance of the information to the claimed invention or the prior art effect of the material described.

Eukaryotic cells store neutral lipids in cytoplasmic lipid droplets[1,2] enclosed in a monolayer of phospholipids and associated proteins[3,4]. These dynamic organelles[5] serve as the principal reservoirs for cellular energy storage and the building blocks for membrane lipids. Excessive lipid accumulation in cells is a central feature of diseases such as obesity, diabetes, and atherosclerosis, yet remarkably little is known about lipid-droplet cell biology. Accordingly, there is a need in the art for a better understanding of the role of lipid droplets in disease.

Rising oil prices and greenhouse emissions have caused a renewed interest in biofuels. Biofuels can be broadly defined as solid, liquid, or gas fuels derived from recently dead biological material, most commonly plants. This distinguishes it from fossil fuel, which is derived from long dead biological material. Biofuels can be theoretically produced from any (biological) carbon source. The most common by far is photosynthetic plants that capture solar energy. Many different plants and plant-derived materials are used for biofuel manufacture. For example, sugar crops (sugar cane, sugar beet, and sweet sorghum) or starch (corn/maize) may be grown and then fermented by yeast to produce ethanol (ethyl alcohol). Alternatively, plants that (naturally) produce oils, such as oil palm, soybean, algae, or jatropha may be grown. When these oils are heated, their viscosity is reduced, and they can be burned directly in a diesel engine, or the oils can be chemically processed to produce fuels such as biodiesel. One of the greatest technical challenges is to develop efficient ways to convert biomass energy into biofuels. In particular, it has been difficult to find sources of biomass that naturally contain a high concentration of oils. Accordingly, there is a need in the art to develop strategies for developing new, oil-rich sources for the production of biofuels.

Specific Patents and Publications

U.S. Pat. No. 7,135,308, issued Nov. 14, 2006 to Bush et al, titled "Process for the production of ethanol from algae," describes a process for the production of ethanol by harvesting starch-accumulating filament-forming or colony-forming algae to form a biomass, initiating cellular decay of the biomass in a dark and anaerobic environment, fermenting the biomass in the presence of a yeast, and the isolating the ethanol produced.

US Patent Application Publication No. 2004/0006792, by Filatti et al, titled "Nucleic acid constructs and methods for producing altered seed oil compositions" discloses recombinant nucleic acid molecules, constructs, and other agents associated with the coordinate manipulation of multiple genes in the fatty acid synthesis pathway. In particular, the agents disclosed there are associated with the simultaneous enhanced expression of certain genes in the fatty acid synthesis pathway and suppressed expression of certain other genes in the same pathway. Also described there are plants incorporating such agents, and in particular plants incorporating such constructs where the plants exhibit altered seed oil compositions. The oil from the plants may be used as a diesel fuel. This application provides guidance for carrying out transformations using the present gene constructs and other teachings below.

US Patent Application Publication No. 2004/0043389, by McCarthy, titled "Methods and compositions for identifying risk factors for abnormal lipid levels and the diseases and disorders associated therewith" provides nucleic acid molecules and methods for using polymorphic regions of DNA that are associated with abnormal lipid levels and associated disorders to determine risk for a disease. This application provides guidance for carrying out diagnostic tests using the present gene constructs and other teachings below.

Work of the present inventors was published by them in *Nature* 453, 657-661 (29 May 2008).

BRIEF SUMMARY OF THE INVENTION

The following brief summary is not intended to include all features and aspects of the present invention, nor does it imply that the invention must include all features and aspects discussed in this summary.

In one embodiment, present invention provides a method of increasing lipid concentration in a eukaryotic cell, comprising increasing or decreasing expression of a gene selected from the genes listed in Table 1, Table 2 or Table 3, or an ortholog thereof. In one aspect of this embodiment, the method comprises decreasing the expression of a gene, or an ortholog thereof, found in phenotypic classes III, IV, or V (see below). As explained in detail below, phenotypic class I refers to a phenotype with fewer lipid droplets. Class II reefers to a phenotype with smaller lipid droplets, which are more dispersed; class III refers to a phenotype with normal or larger size lipid droplets which are more dispersed; class IV refers to a phenotype with normal or larger size lipid droplets which are more condensed; and class V refers to a phenotype with fewer lipid droplets, but with larger size. The present method of altered phenotype creation may be accomplished using any technique known in the art, including but not limited to transfecting the cell with a vector that expresses RNA interference (RNAi), or small hairpin RNA (shRNA) that targets the gene. This may be used to reduce gene expression to produce a class III-V phenotype, having higher lipid content. In another aspect of this embodiment, the method comprises increasing expression of a gene, or an ortholog thereof, found in phenotypic classes I or II (see below). This may be accomplished by any technique known in the art, including but not limited to transfecting the cell with a construct containing a gene found in phenotypic classes I or II.

Any eukaryotic cell may be the target of the present invention. In a preferred aspect of this embodiment the cell is a plant cell, where the plant may be, for example, soy, coconut, corn, cotton, flax, palm, rapeseed, canola, safflower, sunflower, or algae. In another embodiment, the eukaryotic cell is a yeast cell or the cell may be cultured cyanobacteria. Algal cells from Micromonas, whose genome is known, may also be used.

Preferably, the cell is used as a raw material for producing, e.g., a biofuel, a cooking oil, or a lubricant. In this case, the method preferably includes extracting the lipids from the cell.

In another embodiment, the present invention provides a method of decreasing lipid concentration in a eukaryotic cell, comprising increasing or decreasing expression of a gene selected from the genes listed in Table 1, 2, or 3, or an ortholog thereof. In one aspect of this embodiment, the method comprises increasing the expression of a gene, or an ortholog thereof, found in phenotypic classes III, IV, or V. This may be accomplished using any technique known in the art, including but not limited to transfecting the cell with a construct containing a gene found in phenotypic classes III, IV, or V. In another of this embodiment, the method comprises decreasing the expression of a gene, or an ortholog thereof, found in phenotypic classes I or II. This may be accomplished using any technique known in the art, including but not limited to transfecting the cell with a vector that expresses RNA interference (RNAi), or small hairpin RNA (shRNA) that targets the gene.

Any eukaryotic cell may be the target of the present invention. In a preferred aspect of this embodiment, the cell is an animal cell from an organism characterized by an excess of lipids, including but not limited to obesity, fatty liver disease, hyperlipidemia, a lipid storage disease, heart disease, and peripheral artery disease.

In yet another embodiment, the present invention provides a method of identifying a diagnostic marker of a disease characterized by an excess of lipids. According to this method, the level of expression of a gene selected from the genes listed in Table 1, 2, or 3, or an ortholog thereof, is compared in organisms with and without the disease. Next, it is determined if there is a difference in the level of expression of said gene in organisms with and without said disease. Finally, if the determination reveals a difference in expression of said gene in organisms with and without said disease, the gene is identified as a diagnostic marker.

BRIEF DESCRIPTION OF THE DRAWINGS

FIG. 1 shows how oleate increases the formation of lipid droplets in *Drosophila* S2 cells.

FIG. 3 is a series of photographs which show effects of Cct1.

FIG. 4 shows that Arf1-COPI complex members function in the formation of lipid droplets. FIG. 4E is a graph showing that Arf79F, Cct1 and double knockdowns lead to decreased glycerol release to the medium. A transgene encoding Arf79F (Q71L) leads to increased release of glycerol. Experiments were as in FIG. 4D, and the glycerol release was measured. Results are means and s.d. for three independent experiments. * indicates P<0.05, and ** indicates P<0.01 versus control RNAi (left) and versus control transgene (right).

DETAILED DESCRIPTION OF THE PREFERRED EMBODIMENT

Definitions

Figure 1A:
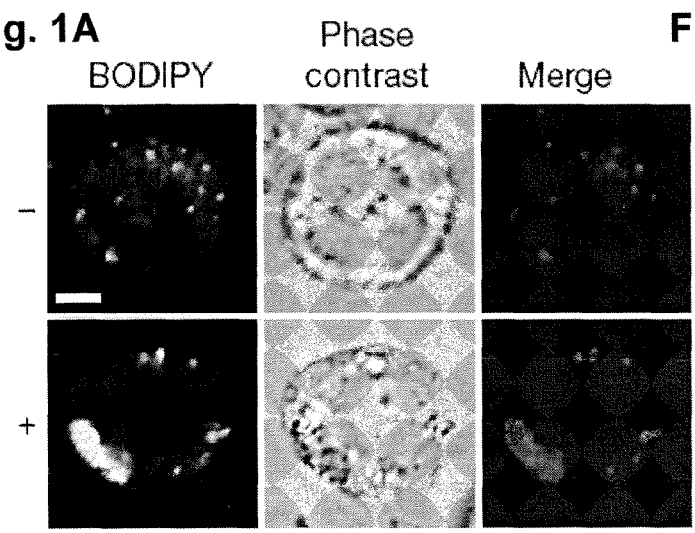
FIG. 1A is series of micrographs of S2 cells incubated for 24 hours without (upper) or with (lower) 1 mM oleate. Staining with BODIPY, phase-contrast image, and overlay are shown.

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification.

As used herein, the term "biofuel" is meant to refer to a variety of fuels made from renewable and inexhaustible biomass resources. These biomass resources include any plant or animal derived organic matter, such as dedicated energy crops and trees, agricultural food and feed crops, agricultural crop wastes and residues, wood wastes and residues, aquatic plants, algae, plant oils, animal oils, animal tissues, animal wastes, municipal wastes, and other waste materials. Biofuels may include, but are not limited to, hydrocarbons, hydrocarbons in the middle distillate range, diesels, kerosenes, gasoline, gasoline fractions, biodiesel, biojet fuel, biogasolines and combinations thereof.

As used herein, the term "plant oil" is meant to refer to lipids derived plant sources, such as agricultural crops and forest products, as well as wastes, effluents and residues from the processing of such materials. Plant oils may include vegetable oils. Examples of plant oils may include, but are not limited to, canola oil, sunflower oil, soybean oil, rapeseed oil, mustard seed oil, palm oil, corn oil, soya oil, linseed oil, peanut oil, coconut oil, corn oil, olive oil, and combinations thereof.

As used herein, the term "lipid" is meant to refer to fatty acids from biological sources and their derivatives, most commonly esters (the reaction product of an organic acid and an alcohol) and amides (the reaction product of an organic acid and an amine). The most common class of lipid is the triglyceride, the ester product of the triple alcohol glycerin (glycerol) with fatty acids.

As used herein, the term "fatty acid" is meant to refer to organic acids synthesized in nature by both animals and plants. They typically contain a hydrocarbon group with 14 to 24 carbon atoms, although chains of 4 to 28 carbons may be found. Longer chains exist, but typically in low concentrations. The hydrocarbon group may be saturated or unsaturated.

As used herein, the term "eukaryotic cell" means a cell having a distinct, membrane-bound nucleus. Such cells may include human, insect or plant cells. Examples of plant cells include microscopic algae such as *Chlamydomonas* (green algae), *Botryococcus braunii*, *Chlorella*, *Dunaliella tertiolecta*, *Gracilaria*, *Pleurochrysis carterae* (also called CCMP647), *Sargassum*, and other marine microalgae suitable for biofuel use.

As used herein, the term "animal oil" is meant to refer to lipids derived animal sources, as well as wastes, effluents and residues from the processing of such materials. Examples of animal oils may include, but are not limited to, animal fats, yellow grease, animal tallow, pork fats, pork oils, chicken fats, chicken oils, mutton fats, mutton oils, beef fats, beef oils, and combinations thereof.

The term "identical" or "identity" in the context of two nucleic acids or polypeptide sequences refers to the residues in the two sequences which are the same when aligned for maximum correspondence. Optimal alignment of sequences for comparison can be conducted, e.g., by the local homology algorithm of Smith and Waterman Adv. Appl. Math. 2: 482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

Identity may also be determined at the amino acid level by comparing gene products from a cell of interest and *Drosophila*. In this case, as applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95, 96, 97, or 98 percent sequence identity, and most preferably at least 99 percent sequence identity. Preferably, residue positions which are not identical differ by conservative amino acid substitutions. As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. Conservative amino acid substitutions are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; phenylalanine, tryptophan, and tyrosine are an aromatic family, and cysteine and methionine as a sulfur-containing side chain family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Preferred conservative amino acid substitution groups are: valine-leucine-isoleucine, phenylalanine-tyrosine, lysine-arginine, alanine-valine, glutamic acid-aspartic acid, cysteine-methionine, and asparagine-glutamine.

Overview

The present invention is based on a discovery, by means of a genome-wide RNA interference (RNAi) screen in *Drosophila* S2 cells, of genes that function in lipid-droplet formation and regulation. The phenotypes of the gene knockdowns sorted into five distinct phenotypic classes. Genes encoding enzymes of phospholipid biosynthesis proved to be determinants of lipid-droplet size and number, suggesting that the phospholipid composition of the monolayer profoundly affects droplet morphology and lipid utilization. A subset of the ARF1/COPI vesicular transport proteins also regulated droplet morphology and utilization, thereby identifying a previously unrecognized function for this machinery. These phenotypes are conserved in mammalian cells, suggesting that insights from these studies are likely to be central to our understanding of human diseases involving excessive lipid storage. In addition, the phenotypes suggest that lipid storage may be deliberately increased, e.g., in plant cells, thus providing an improved raw material for the production of biofuels, cooking oils, and lubricants.

Figure 1B:
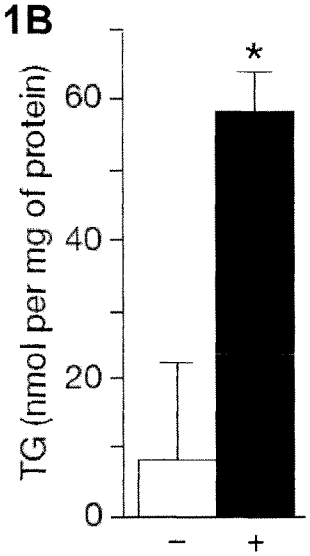
FIG. 1B is a graph showing that oleate-loaded cells have an increased triacylglycerol (TG) content. Cells were incubated as in FIG. 1a and their TG (triglyceride) contents were measured. Results are means and s.d. for three experiments; P<0.05.

Lipid-droplet formation in *Drosophila* Schneider 2 (S2) cells is an excellent system for functional genomic studies with efficient gene inactivation by RNAi[6]. In the exemplified methods below, lipid-droplet formation was induced by incubation with 1 mM oleate for 24 hours. Staining with BODIPY showed droplet size, number, and overall volume were increased (FIG. 1A); cellular triacylgylcerol (TG) content increased sevenfold (FIG. 1B). BODIPY-stained fluorescent signals corresponded to lipid droplets with a red fluorescent protein mCherry[7] fused with LSD1, which localizes exclusively to the surface of lipid droplets[3] (not shown).

Figure 1C:
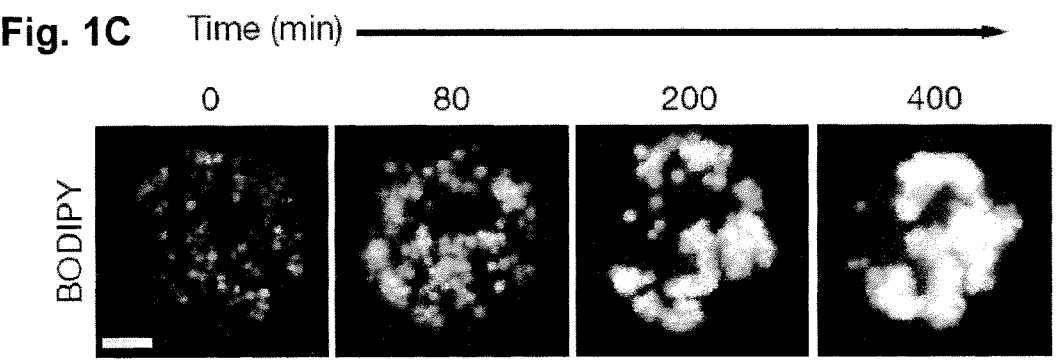
FIG. 1C is a series of micrographs showing that lipid droplet formation occurs in steps. Single cells were followed by four-dimensional confocal time-lapse photography. Representative maximum projections of three-dimensional stacks at the indicated times are shown. Scale bar is 3 μm.
Figure 1D:
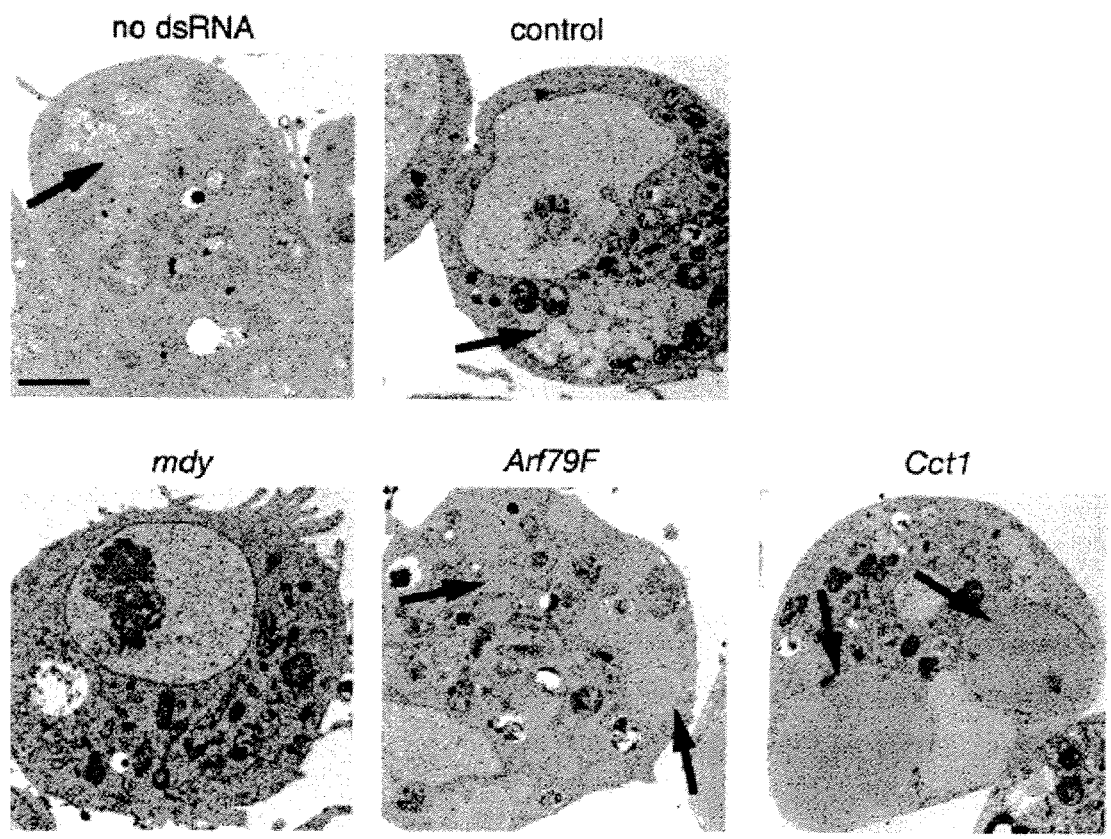
FIG. 1D shows electron micrographs confirming tight clustering of droplets in mdy, Arf79F and Cct1 knocked-out *Drosophila* S2 cells.

Imaging this process by time-lapse microscopy of BODIPY-labeled cells after oleate addition showed that droplet formation occurred in a stepwise manner (FIG. 1C). First, increased numbers of small droplets formed in dispersed locations throughout the cell. Next, droplets increased in size and finally aggregated into one or several large clusters, resembling grapes. Electron microscopy confirmed the tight clustering of the droplets, which were often near the nucleus (FIG. 1D).

Figure 2A:
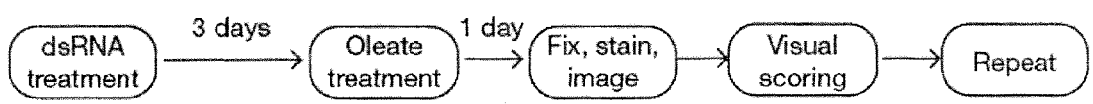
FIG. 2A shows an outline for the strategy to screen for genes involved in lipid-droplet biogenesis.

To unravel the molecular mechanisms governing this progression of changes during lipid-droplet formation, a genome-wide RNAi screen in S2 cells (FIG. 2A) was carried out. Images were acquired and examined by two independent observers, who scored them for alterations in droplet number, size, and dispersion. The same data were analyzed computationally. From visual screening, both observers identified 847 candidate genes with altered lipid-droplet morphology. To verify these genes and to minimize misidentification of genes from off-target effects of RNAi treatments[8,9], RNAi experiments for these genes were repeated with a second, distinct set of dsRNAs[10]. Visual analyses identified 132 genes whose knockdown consistently and repeatedly altered lipid-droplet morphology (Table 1 below) and an additional 48 genes for which knockdown phenotypes were scored in two of three rounds (Table 2 below). Computational analysis confirmed 86 of these 180 genes and added 47 genes with altered lipid-droplet morphology (Table 3 below). Thus, identified 227 genes in total were identified (~1.5% of the genome) that affect lipid-droplet morphology. The high stringency of the criteria used, however, may have caused omission of some genes involved in lipid droplet morphology.

TABLE 1

Genes with dramatically altered lipid droplet morphology identified in screen

| CG# | Symbol | Function |
|---|---|---|
| Class I Fewer lipid droplets | | |
| CG10370 | Tbp-1 | endopeptidase activity ("proteosome") |
| CG31991 | mdy | diacylglycerol O-acyltransferase activity |
| CG1395 | stg | protein tyrosine/serine/threonine phosphatase activity |
| CG5363 | cdc2 | cyclin-dependent protein kinase activity |
| CG5940 | CycA | cyclin-dependent protein kinase regulator activity |
| CG8975 | RnrS | ribonucleoside-diphosphate reductase activity |
| CG10484 | Dox-A2 | endopeptidase activity ("proteosome") |
| CG4904 | Pros35 | endopeptidase activity ("proteosome") |
| CG3329 | Prosbeta2 | endopeptidase activity; threonine endopeptidase activity |
| CG10938 | ProsMA5 | endopeptidase activity ("proteosome") |
| CG7762 | Rpn1 | endopeptidase activity ("proteosome") |
| CG 1341 | Rptl | endopeptidase activity; ATPase activity ("proteosome") |
| CG16916 | Rpt3 | endopeptidase activity ("proteosome") |
| CG3455 | Rpt4 | endopeptidase activity ("proteosome") |
| CG3328 | | caspase activity |
| CG7425 | eff | ubiquitin-protein ligase activity |
| CG32744 | Ubi-p5E | protein binding |

TABLE 1-continued

Genes with dramatically altered lipid droplet morphology identified in screen

| CG# | Symbol | Function |
|---|---|---|
| CG7292 | Rrp6 | 3'-5' exonuclease activity |
| CG32782 | tlk | protein serine/threonine kinase activity |
| CG8877 | prp8 | RNA splicing factor activity ("spliceosome") |
| CG5352 | 5mB | RNA splicing factor activity ("spliceosome") |
| CG10753 | snRNP69D | RNA splicing factor activity ("spliceosome") |
| CG1249 |  | RNA splicing factor activity ("spliceosome") |
| CG4849 | eEF2 | translation elongation factor activity |
| CG14641 |  | mRNA binding; nucleic acid binding |
| CG3578 | bi | RNA polymerase II transcription factor activity |
| CG7951 | sima | RNA polymerase II transcription factor activity |
| CG7552 | CG33967 | unknown |
| Class II Smaller size lipid droplets, more dispersed | | |
| CG10859 |  | motor activity; dynein complex |
| CG10822 |  | ATPase activity, coupled; dynein complex |
| CG8732 | *1(2)44DEa | long-chain-fatty-acid-CoA ligase activity ("FACS') |
| CG8055 | shrb | carrier activity |
| CG4916 | me31B | ATP-dependent RNA helicase activity |
| CG6718 |  | calcium-independent phospholipase A2 activity |
| CG1318 | Hexo1 | beta-N-acetylhexosaminidase activity; hydrolase activity |
| CG1100 | Rpn5 | endopeptidase activity |
| CG9454 |  | serine-type endopeptidase inhibitor activity |
| CG5119 | *pAbp | poly(A) binding |
| CG11276 | *RpS4 | structural constituent of ribosome; nucleic acid binding |
| CG6501 | Ngp | GTP binding; receptor binding |
| CG31196 | 14-3-3epsilon | DAG-activated phospholipid-dep. protein kinase C inhibitor |
| CG3889 | CSN1b | small GTPase regulator activity; signalsome |
| CG18332 | CSN3 | unknown; signalsome |
| CG2038 | CSN7 | unknown; signalsome |
| CG5179 | Cdk9 | cyclin-dependent protein kinase activity |
| CG7035 | Cbp80 | RNA cap binding |
| CG3180 | RpII140 | DNA-directed RNA polymerase activity |
| CG7885 | RpII33 | DNA-directed RNA polymerase activity |
| CG6711 | Taf2 | RNA polymerase II transcription factor activity |
| CG7957 | MED17 | RNA polymerase II transcription mediator activity |
| CG13867 | MED8 | RNA polymerase II transcription mediator activity |
| CG18009 | Trf2 | RNA polymerase II transcription factor activity |
| CG1343 | Spl | RNA polymerase II transcription factor activity |
| CG7664 | crp | RNA polymerase II transcription factor activity |
| CG31666 |  | transcription factor activity |
| CG2252 | fs(1) h | DNA binding; protein kinase activity |
| CG4817 | Ssrp | single-stranded DNA binding; single-stranded RNA binding |
| CG9007 |  | protein binding; zinc ion binding |
| CG4429 | Rbp2 | translation initiation factor activity; mRNA binding |
| CG9075 | eIF-4a | translation initiation factor activity |
| CG9677 | Int6 | translation initiation factor activity |
| CG9769 | eIF3-S5 | translation initiation factor activity |
| CG32104 |  | ATP binding; ATPase activity; calcium ion binding |
| CG1715 | 1(3)03670 | unknown |
| CG6729 |  | unknown |
| CG9170 |  | unknown |
| CG9578 |  | unknown |
| CG10933 |  | unknown |
| CG14220 |  | unknown |
| CG15009 | ImpL2 | unknown |
| Class III Normal/larger size lipid droplets, more dispersed | | |
| CG8385 | Arf79F | GTP binding; GTPase activity |
| CG8487 | garz | ARF guanyl-nucleotide exchange factor activity |
| CG7961 | alpha Cop | binding; protein transporter activity; COPI complex |
| CG6223 | betaCop | binding; COPI complex |
| CG6699 | beta'Cop | protein transporter activity; COPI complex |
| CG14813 | deltaCOP | COPI complex |
| CG1528 | gammaCop | binding; COPI complex |
| CG3948 | zetaCOP | COPI complex |
| Class IV Normal/larger size lipid droplets, highly condensed | | |
| CG8053 | eIF-1A | translation initiation factor activity ("eIF") |
| CG4153 | eIF-2beta | translation initiation factor activity ("eIF") |
| CG8636 | eIF3-S4 | translation initiation factor activity ("eIF") |
| CG4954 | eIF3-S8 | translation initiation factor activity ("eIF") |
| CG4878 | eIF3-S9 | translation initiation factor activity ("eIF") |
| CG7490 | RpLPO | DNA-(apurinic or apyrimidinic site) lyase activity; ribosome |
| CG5844 |  | hydro-lyase activity; oxidoreductase activity |

TABLE 1-continued

Genes with dramatically altered lipid droplet morphology identified in screen

| CG# | Symbol | Function |
|---|---|---|
| Class V Fewer lipid droplets, larger size | | |
| CG1049 | Cct1 | choline-phosphate cytidylyltransferase activity |
| CG18330 | Cct2 | choline-phosphate cytidylyltransferase activity |
| CG2201 | CK | choline kinase activity; ethanolamine kinase activity |
| CG8522 | HLH106 | transcription factor activity; SREBP |
| CG33131 | SCAP | sterol regulatory element binding-protein (SREBP) cleavage |
| CG3523 | FAS | fatty-acid synthase activity |
| Ribosomal protein encoding genes | | |
| CG12275 | RpS10a | structural constituent of ribosome; nucleic acid binding |
| CG8332 | *RpS15 | structural constituent of ribosome; nucleic acid binding |
| CG8922 | RpS15a | structural constituent of ribosome; nucleic acid binding |
| CG12324 | *RpS15Ab | structural constituent of ribosome; nucleic acid binding |
| CG8900 | *RpS18 | structural constituent of ribosome; nucleic acid binding |
| CG15693 | *RpS20 | structural constituent of ribosome; nucleic acid binding |
| CG15697 | RpS30 | structural constituent of ribosome; nucleic acid binding |
| CG14792 | sta | structural constituent of ribosome; nucleic acid binding |
| CG8857 | RpS11 | structural constituent of ribosome; nucleic acid binding |
| CG2033 | *RpS15Aa | structural constituent of ribosome; nucleic acid binding |
| CG4046 | *RpS16 | structural constituent of ribosome; nucleic acid binding |
| CG3922 | *RpS17 | structural constituent of ribosome; nucleic acid binding |
| CG4464 | *RpS19a | structural constituent of ribosome; nucleic acid binding |
| CG8415 | RpS23 | structural constituent of ribosome; nucleic acid binding |
| CG3751 | RpS24 | structural constituent of ribosome; nucleic acid binding |
| CG6779 | *RpS3 | DNA-(apurinic or apyrimidinic site) lyase activity; ribosome |
| CG2168 | *RpS3A | structural constituent of ribosome; nucleic acid binding |
| CG10944 | *RpS6 | structural constituent of ribosome; nucleic acid binding |
| CG7808 | *RpS8 | structural constituent of ribosome; nucleic acid binding |
| CG5920 | *sop | structural constituent of ribosome; nucleic acid binding |
| CG17521 | RpL10 | structural constituent of ribosome; nucleic acid binding |
| CG7283 | RpL10Ab | structural constituent of ribosome; nucleic acid binding |
| CG4651 | *RpL13 | structural constituent of ribosome; nucleic acid binding |
| CG1475 | RpL13A | structural constituent of ribosome; nucleic acid binding |
| CG3203 | RpL17 | structural constituent of ribosome; nucleic acid binding |
| CG8615 | RpL18 | structural constituent of ribosome; nucleic acid binding |
| CG6846 | RpL26 | structural constituent of ribosome; nucleic acid binding |
| CG4759 | RpL27 | structural constituent of ribosome; nucleic acid binding |
| CG15442 | RpL27A | structural constituent of ribosome; nucleic acid binding |
| CG12740 | RpL28 | structural constituent of ribosome; nucleic acid binding |
| CG1821 | RpL31 | structural constituent of ribosome; nucleic acid binding |
| CG7939 | RpL32 | structural constituent of ribosome; nucleic acid binding |
| CG4111 | *RpL35 | structural constituent of ribosome; nucleic acid binding |
| CG7622 | RpL36 | structural constituent of ribosome; nucleic acid binding |
| CG5502 | *RpL4 | structural constituent of ribosome; nucleic acid binding |
| CG2960 | RpL40 | structural constituent of ribosome; nucleic acid binding |
| CG11522 | RpL6 | structural constituent of ribosome; nucleic acid binding |
| CG4897 | RpL7 | structural constituent of ribosome; nucleic acid binding |
| CG3314 | RpL7A | structural constituent of ribosome; nucleic acid binding |
| CG1263 | RpL8 | structural constituent of ribosome; nucleic acid binding |
| CG6141 | RpL9 | structural constituent of ribosome; nucleic acid binding |

TABLE 2

Genes with moderately altered lipid droplet morphology identified in screen

| CG# | Symbol | Function |
|---|---|---|
| Class I Fewer lipid droplets | | |
| CG3938 | CycE | cyclin-dependent protein kinase regulator activity |
| CG10800 | Rcal | unknown |
| CG11888 | Rpn2 | endopeptidase activity |
| CG1404 | *ran | GTPase activity; protein binding; GTP binding |
| CG16792 | DebB | RNA splicing factor activity |
| CG2189 | Dfd | RNA polymerase II transcription factor activity |
| CG8264 | Bx42 | unknown |
| CG12750 | ncm | unknown |
| Class II More lipid droplets, smaller size and more dispersed | | |
| CG3887 | | selenium binding |
| CG12235 | Arp 11 | structural constituent of cytoskeleton; actin binding |
| CG9750 | rept | DNA helicase activity |
| CG17821 | | acyltransferase activity |
| CG17654 | Eno | phosphopyruvate hydratase activity |
| CG9595 | osm-6 | microtubule motor activity; kinesin complex |
| CG7033 | * | ATPase activity, coupled; unfolded protein binding |
| CG3018 | Iwr | ubiquitin-protein ligase activity |
| CG4320 | raptor | binding; protein modification |

TABLE 2-continued

Genes with moderately altered lipid droplet morphology identified in screen

| CG# | Symbol | Function |
|---|---|---|
| CG11622 | Rlip | Ral GTPase activator activity |
| CG4012 | gek | protein serine/threonine kinase activity; small GTPase regulator |
| CG4700 | Sema-2a | receptor activity |
| CG8606 | RhoGEF4 | Rho guanyl-nucleotide exchange factor activity |
| CG11870 | | protein serine/threonine kinase activity |
| CG12344 | | GABA receptor activity |
| CG13995 | | G-protein coupled receptor activity |
| CG17060 | Rab10 | GTPase activity |
| CG9575 | *Rab35 | GTPase activity |
| CG6197 | | transcription regulator activity |
| CG11266 | | mRNA binding; nucleotide binding |
| CG12267 | | DNA-directed RNA polymerase activity |
| CG12254 | MED25 | RNA polymerase II transcription mediator activity |
| CG3886 | Psc | transcription regulator activity |
| CG11799 | Mnf | transcription factor activity |
| CG17328 | | transcription regulator activity |
| CG10986 | g | binding; intracellular transport |
| CG7861 | | protein folding |
| CG9636 | | unknown |
| CG8087 | | unknown |
| CG9432 | l(2)01289 | protein disulfide isomerase activity |
| CG13605 | | protein binding; zinc ion binding |
| CG31386 | | unknown |
| CG1524 | RpS14a | structural constituent of ribosome; nucleic acid binding |
| CG8495 | RpS29 | structural constituent of ribosome; nucleic acid binding |

TABLE 3

Genes identified in screen by automated analysis

| CG# | Note | Symbol | Function |
|---|---|---|---|
| CG17608 | T | fu12 | l-acylglycerol-3-phosphate O-acyltransferase activity |
| CG9390 | T | AcCoAS | acetate-CoA ligase activity |
| CG7379 | C | | acetyltransferase activity; protein binding |
| CG10996 | M | | aldose l-epimerase activity |
| CG9143 | C | | ATP-dependent RNA helicase activity |
| CG32465 | T | CG34127 | carboxylesterase activity |
| CG7094 | T | | casein kinase I activity |
| CG5452 | M | dnk | deoxynucleoside kinase activity; ATP binding |
| CG16713 | T | | erine-type endopeptidase inhibitor activity |
| CG7440 | T, M, C | tgy | galactosyltransferase activity |
| CG9042 | | Gpdh | glycerol-3-phosphate dehydrogenase (NAD+) activity |
| CG12530 | | Cdc42 | GTPase activity |
| CG8287 | | Rab8 | GTPase activity |
| CG3949 | | hoip | mRNA binding; structural constituent of ribosome |
| CG11027 | | Arf102F | NAD(P)+-protein-arginine ADP-ribosyltransferase activity |
| CG7368 | | | nucleic acid binding; zinc ion binding |
| CG7054 | | | phosphatidylethanolamine binding; kinase inhibitor activity |
| CG9060 | | Zpr1 | protein binding; zinc ion binding |
| CG1210 | | Pk61C | protein serine/threonine kinase activity |
| CG9635 | | RhoGEF2 | Rho guanyl-nucleotide exchange factor activity |
| CG7269 | | Hel25E | RNA helicase activity |
| CG7577 | | ppk20 | serine-type peptidase activity |
| CG7352 | | | structural constituent of cytoskeleton |
| CG7627 | | | ATPase activity; transporter activity |
| CG15319 | | nej | transcription coactivator activity; acetyltransferase activity |
| CG6964 | | Gug | transcription corepressor activity |
| CG17888 | | Pdpl | transcription factor activity |
| CG7734 | | shn | transcription factor activity |
| CG9954 | | maf-S | transcription factor activity |
| CG10543 | | | transcription regulator activity |
| CG7036 | | mo | transcription regulator activity |
| CG7372 | | | transcription regulator activity |
| CG8950 | | | transcription regulator activity |
| CG2238 | | Ef2b | translation elongation factor activity |
| CG9596 | | | translation initiation factor activity |
| CG7375 | | | ubiquitin-protein ligase activity |
| CGl1132 | | DMAP1 | unknown |
| CG16783 | | fzr2 | unknown |
| CG30118 | | | unknown |
| CG3885 | | sec3 | unknown |
| CG5114 | | | unknown |
| CG5308 | | dpr5 | unknown |
| CG7085 | T | l(2)s5379 | unknown |
| CG7946 | T | | unknown |
| CG8309 | T | Tango7 | unknown |
| CG9047 | T | | unknown |
| CG9422 | T | | unknown |

Figure 2B:
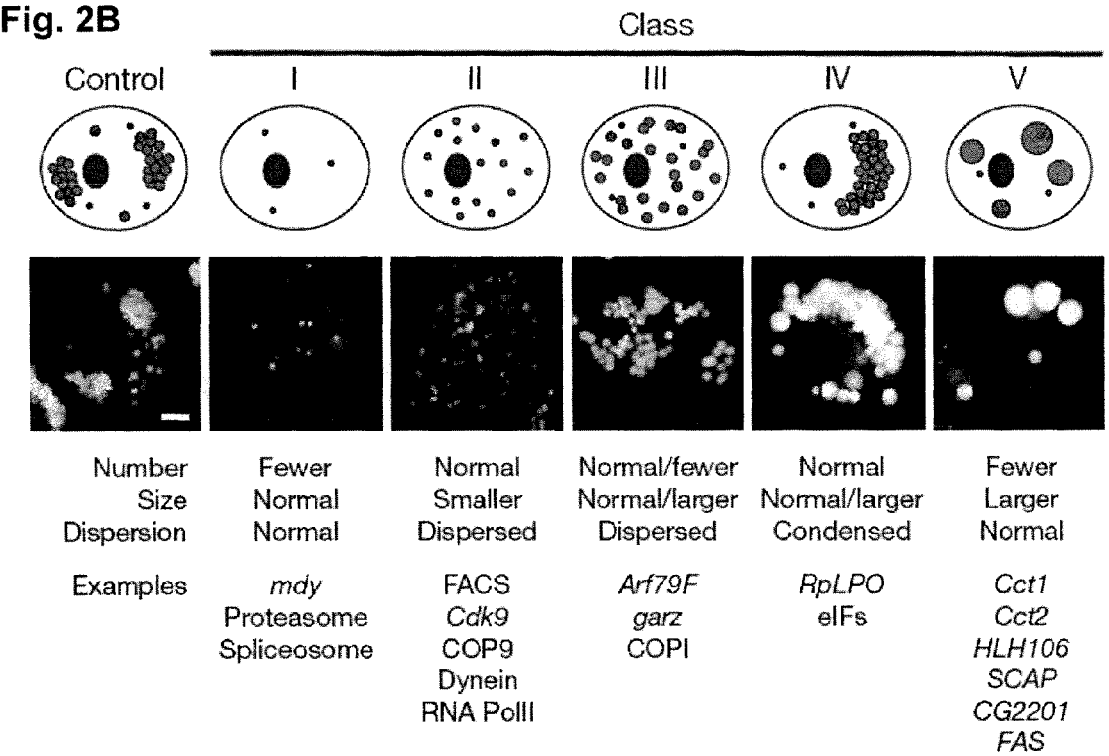
FIG. 2B shows that genes involved in the screen for lipid-droplet biogenesis fall into distinct phenotypic classes. The 132 most striking phenotypes were classified according to lipid-droplet number, size, and dispersion. From this classification, five major classes emerged; a graphic representation (top), an example image (middle) and some examples (bottom) are shown. Scale bar is 3 μm.

The above Table 1 may be characterized as listing five classes of genes, classes I-V, as illustrated in FIG. 2B. As indicated there, the classes correspond to different phenotypes created by the knock down of the listed genes. Thus it is shown that preventing expression of certain types of genes has a marked effect on lipid droplet formation. These genes are divided into phenotypic classes, based on visible observation, which has been shown to correlate to actual lipid concentrations and content in affected cells. Asterisks indicate genes previously identified from the Drosphila embryonic lipid droplet proteome[37].

Class I genes include genes having endopeptidase activity, termed "proteosome genes" in FIG. 2B. Thus, the term "proteosome genes" refers to Tbp-1, Doxc-A2, Pros35, Pros-beta2, ProsMA5, Rpn1, Rpt1, Rpt3 and RPt4. Class I further includes genes having RNA splicing factor activity termed in FIG. 2B "spliceosome genes." These genes are prp8, smB, and snRP69D.

Class II genes include FACS, cdk9, COP9, dynein, and RNA pol I genes. FACS is gene symbol I(2)44DEa, involved in long chain fatty-acid-CoA ligase activity. COP9 is, as is known, part of the COP9 signalsome complex (see Trends Cell Biol. October 2001;11(10):420-6).

Class III genes include those of the ARF/COPI complex. As is known, ADP-ribosylation factor (ARF) is involved in recruitment of COPI. The classical COPI coat consists of seven coatomer subunits: αCOP, βCOP, β' COP, γCOP, δ COP, ε COP, and ζCOP, as well as the Arf1 small GTPase, which are conserved from yeast to mammals.

Class IV genes include eIFs and RpLPO. EIFs are those indicated in Table 1 as having translation initiation factor activity. Specific eIF sequences can be obtained by searching eIF with a wild card in Flybase.

Class V genes include, as listed in FIG. 2B, cct1, cct2, HLH106 (SREBP), SCAP, CK (cg2201) and FAS.

The work described below was carried out with a eukaryotic (Drosophila) cell line. These cells were grown in a cell culture. Other cell cultures may be used, as appropriate for the biofuel producing species of interest. It is known that Drosphila genes have numerous orthologs in other species. Drosophila genes are overall about 80% conserved in humans. Thus there are described here cell lines having genetically altered expression level of a gene whose alteration has a visible phenotypic effect on either or both of (a) lipid droplet size or (b) lipid droplet number in cells in said cell line. In class I, reducing expression of a gene results in fewer lipid droplets, and class I includes mdy, proteosome genes and spliceosome genes. Mdy, or midway, is known to be homologous to human Dgat genes (e.g. acyl CoA:diacylglycerol acyltransferase −1), known to be involved in lipid metabolism. In class II, reduced gene expression results in smaller, dispersed droplets. These genes include FACS, cdk9, COP9, dynein, and RNA Pol I. In class III, reduced gene expression results in larger, dispersed lipid droplets. These genes include arf-COPI genes and garz. The term "arf-COPI" refers to arf genes and COPI genes, which are functionally related. Any DNA or amino acid sequence encoding or encoded by a gene identified here may be obtained from Flybase, the repository of the Drosophila genome project. For example, by entering "arf" in Flybase, one retrieves sequences for arf72A, arf79F and AARF84F. Of these, ARF79F is preferred as a gene to be modulated according to the present invention. By entering "COPI," one obtains the sequence for deltaCOP. In class IV, reduced gene expression results in larger, condensed lipid droplets. These genes include RpLPO and the eIFs (translation initiation factors). In class V, reduced gene expression results in fewer, larger lipid droplets. These genes include cct1, cct2, HLH106, SCAP, CG2201 and FAS.

Carrying out the present methods in cells other than Drosophila cells is described in Example 2. Overall, one first selects a gene as identified here, e.g., mdy (which will be increased to increase lipid concentration) or cct1 or ARF79F (which will be decreased to increase lipid concentration). Multiple transgenes or transgene/knock out combinations can be used in a single cell culture. The sequence of any gene listed here may be obtained from NCBI Entrez gene by entering the gene name. One may use this sequence to search for orthologs, using Pfam (pfam.sanger.ac.uk). One then obtains the occurrence of the sequence or subsequence searched as aligned with different species. Mdy was found to have entries in UNiProt for Drosophila and yeast. These sequences may be used directly as transgenes and/or used to query for orthologs. Any sequence could be used as a query sequence. Numerous other methods may be used. Flybase also contains listings of known orthologs, including yeast and Arabidopsis thaliana (Arabidopsis). If the sequence is not found in a database, a cDNA or genomic library of the organism of interest is prepared. Then the Drosophila sequence of the gene to be modified (e.g., Mdy, cct1, ARF79F or the like) is used as a probe to obtain the sequence of interest from the organism of interest. One may design degenerate probes and/or use low stringency conditions to find near matches in the library. Another method involves comparative genome analysis, as described in Itoh et al., "Curated genome annotation of Oryza sativa ssp. japonica and comparative genome analysis with Arabidopsis thaliana," Genome Research 2007 17:175-183. Using one of these methods, one selects the sequence of interest in the organism of interest. By engineering an algal cell, an algal cell culture may be propagated, as described in more detail e.g. in U.S. Pat. No. 4,324,067, "Algal Cell Harvesting."

Once the sequence of the gene of interest in the organism of interest is in hand, preparing a transgene or a knock out or knock down construct is accomplished as is known in the art. One may knock out the gene by homologous recombination. One may prevent translation of the gene by use of RNA interference or antisense DNA peptide nucleic acids or the like. Knockdown with dsRNA is exemplified here. Further details on gene silencing are set forth in U.S. Pat. No. 7,294,504 to Wang, issued Nov. 13, 2007, entitled "Methods and compositions for DNA mediated gene silencing." For engineering organisms useful in producing biofuel, one chooses methods appropriate to the host organism. For example, a method for introducing foreign genes into green algae utilizing T-DNA of agrobacterium is described in Ausich, EP 19830306603. The desired foreign gene or genes can be inserted into the T-DNA using gene splicing procedures known in the art. One such procedure is described in Garfinkel, David J., et al., "Genetic Analysis of Crown Gall: Five Structure Map of the T-DNA by Site-Directed Mutagenesis," Cell, vol. 27, pp. 143-153, November, 1981. Exemplified there are green alga Chlamydomonas reinhardtii, Protosiphon botryoides (Cambridge Culture Collection 731/1a), and blue-green alga Anacystis nidulans (ATCC 27344). Allnutt et al. "Methods and tools for transformation of eukaryotic algae," U.S. Pat. No. 6,027,900 describes genetic fusions for use in genetic engineering of eukaryotic algae which employ a promoter from a light harvesting protein fused to a protein of interest. Transformed cells are produced by introducing exogenous DNA into a population of target cells and selecting the cells which have taken up the exogenous DNA, usually by measuring expression of some determinant present on the exogenous DNA but missing from the untransformed cells. Transformation of algae and marine organisms is complicated by lack of selection systems which are effective in salt water media. The difficulty is overcome in accordance with this issued US patent by using zeocin resistance as a selective marker, because resistance to zeocin (and related antibiotics) has been discovered to be maintained in high salt medium to a much greater extent than is observed for other antibiotic resistance genes. In growing the engineered cells, one employs a high lipid feedstock, as described in the examples below.

A subset of the most striking genes (41 of the 132) encoded ribosome components and associated proteins. These genes showed a distinct phenotype with more dispersed droplets similar to Class III. However, phase contrast images of these knockdowns revealed decreased cell numbers and multiple large vacuolar structures throughout the cells, suggesting that the cells may not be healthy. It is presently not clear whether these genes involved in protein synthesis are directly involved in lipid droplet biology, or whether their knockdowns result in a non-specific effect on cell viability.

The 132 genes with striking phenotypes were categorized into five distinct phenotypic classes (FIG. 2B and Table 1 above), which were validated for selected knockdowns by electron microscopy (FIG. 1D). The sketches in FIG. 2B illustrate graphically the changes in lipid droplet concentration and size in the different classes assigned here. Class I genes showed reduced numbers of droplets and included midway, a diacylglycerol acyltransferase, subunits of the proteasome and the spliceosome, and several uncharacterized open reading frames. Class II genes gave smaller more dispersed droplets and included subunits of the COP9/signalosome complex, dynein, and RNA polymerase II subunits. Class III genes showed more dispersed droplets of slightly larger size and were members of the ARF1/COPI vesicular transport machinery. Class II included garz. Class IV genes yielded highly condensed clusters of droplets and included members of the translational machinery, RpLPO (large ribosomal protein) and eIFs (translation initiation factors—see *J. Biol. Chem.*, Vol. 267, Issue 28, 20444-20450, 10, 1992). Class V genes contained one or a few very large droplets and included an ortholog of sterol regulatory element binding-protein (SREBP), a master transcriptional regulator of lipid metabolism, and SREBP cleavage activating protein (SCAP)[11]. In *Drosophila*, the SREBP pathway is sensitive to and regulates phospholipid biosynthesis[12]. Intriguingly, this class also included Cct1 and Cct2, which encode isoforms of phosphocholine cytidylyltransferase, the enzyme that catalyzes the rate-limiting step in phosphatidylcholine (PC) synthesis[13], and CG2201, which is predicted to have choline kinase activity that phosphorylates and activates choline[14]. Thus, most Class V genes were linked directly or indirectly to phospholipid biosynthesis.

Figure 3A:
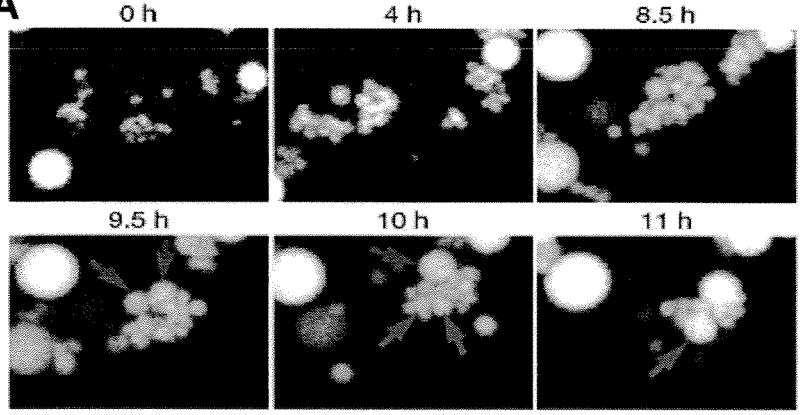
FIG. 3A shows micrographs of lipid-droplet formation induced by oleate in Cct1 knockdown cells (FIG. 3A). Single cells were followed by time-lapse confocal microscopy. Representative projections revealed that droplets first proliferate normally (upper) and then fuse (lower). Examples of fusion are indicated by arrows.
Figure 3B:
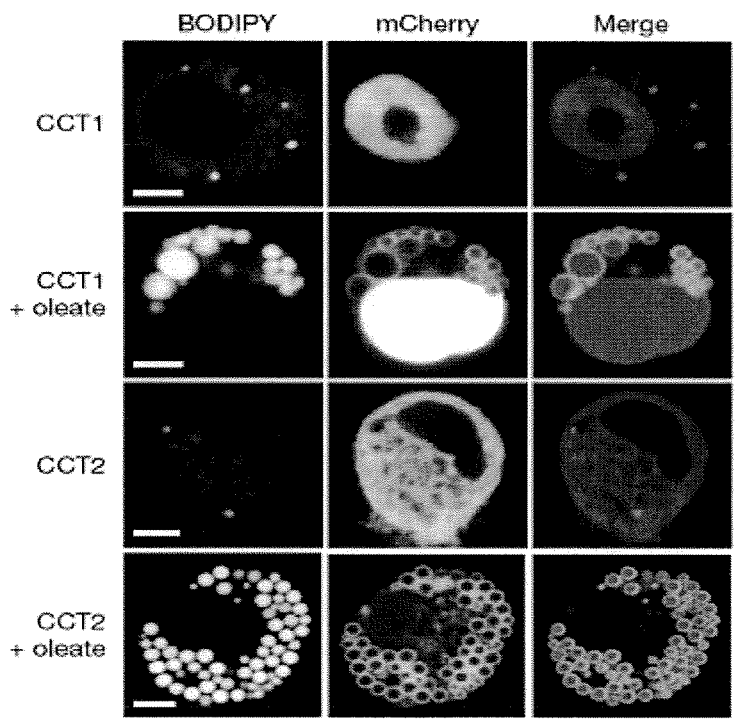
FIG. 3B is a series of micrographs showing that CCT enzymes localize to the surface of droplets after induction with oleate. Cct1 and Cct2 were transiently expressed in S2 cells as amino-terminal mCherry-tagged fusion proteins and were stained and imaged before or after induction. BODIPY staining, mCherry fluorescence, and merge are shown. Scale bar is 3 μm.
Figure 3C:
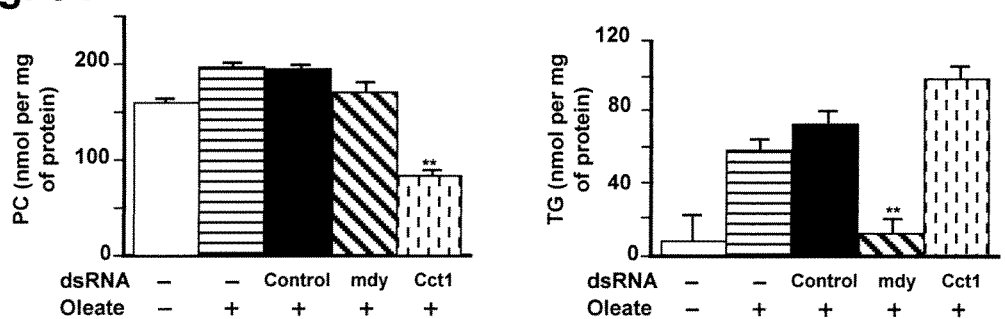
FIG. 3C shows graphs indicating that knockdown cells have less phosphatidylcholine (PC) and more triacylgycerol (TG). S2 cells were treated with dsRNAs as indicated, loaded with oleate (as in FIG. 1a) and lysed. PC (left) and TG (right) levels in the extract were measured. Results are means and s.d. for three independent experiments. **, P<0.01 versus control RNAi.
Figure 3D:
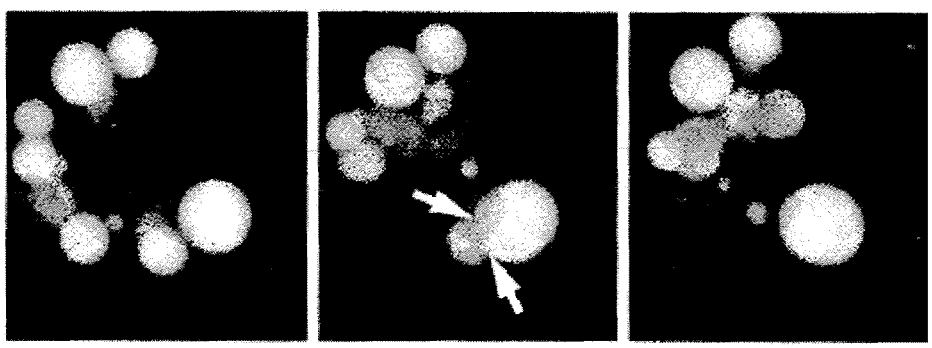
FIG. 3D shows micrographs demonstrating lipid droplet fusion.

To further explore how phospholipid metabolism regulates lipid-droplet formation, we characterized the Cct1 and Cct2 knockdowns. Larger droplets in Cct knockdowns could arise from a failure to form new droplets, forcing newly synthesized neutral lipids into a few large droplets, or from fusion of independently formed droplets. To distinguish these possibilities, we visualized the dynamics of lipid-droplet formation by time-lapse microscopy and found evidence that the droplets fuse (FIG. 3A and FIG. 3D).

We then examined where CCT proteins act. In untreated cells, mCherry-tagged CCT1 localized exclusively to the nucleus (FIG. 3B), similar to mammalian cytidyltransferase (CT-α)[13,15]. After oleate treatment, a significant portion of CCT1 localized to the lipid-droplet surface. By contrast, similarly tagged CCT2 localized to the cytoplasm, but also was concentrated on droplet surfaces after oleate treatment. This dramatic translocation of CCT enzymes to the droplet surface may serve to provide adequate phosphatidylcholine (PC) to the phospholipid monolayers of growing lipid droplets. If so, the ratio of surface phospholipids to core neutral lipids may regulate lipid-droplet morphology: when phospholipids are limiting (as in Cct1 or Cct2 knockdowns), fusion is induced to reduce the surface-to-volume ratio of droplets. In fact, the content of PC in cells with Cct1 knockdown was reduced by ~60% (FIG. 3C, left panel), and the TG content was increased by ~40% (FIG. 3C, right panel). The increase in TG may reflect compensatory channeling of diacylglycerol into neutral lipids. A reduced PC content would increase the relative amount of phosphatidylethanolamine in the droplet monolayer (as observed in flies lacking Cct1[16]), which itself may directly promote droplet fusion[17]. Without wishing to be bound by any scientific theory, the present results suggest a model posing that PC availability is a crucial regulator of lipid-droplet size and number.

Figure 4A:
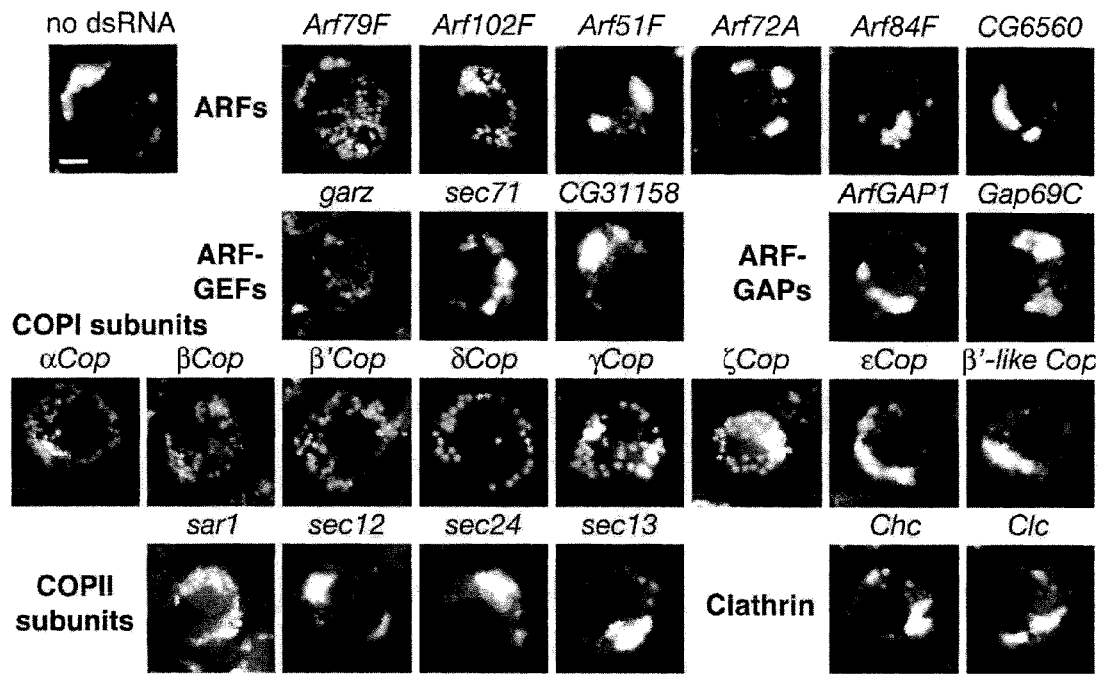
FIG. 4A is a series of micrographs showing that knockdowns of Arf79F, the GEF gene gartenzwerg (garz) and specific subunits of the COPI coat affect lipid-droplet formation similarly. Representative images are shown. Controls included knockdowns of COP II (sar1, sec12, sec24 and sec13), clathrin (Che and Cle), other ARFs (ARF4: Arf102F, ARF6: Aif5IF, ARL1: Arf72A, ARL2: Arf84F and ARL3: CG6560), GEFs (sec71 and CG31158) and GAPs (ArfGAP1 and Gap69C).
Figure 4B:
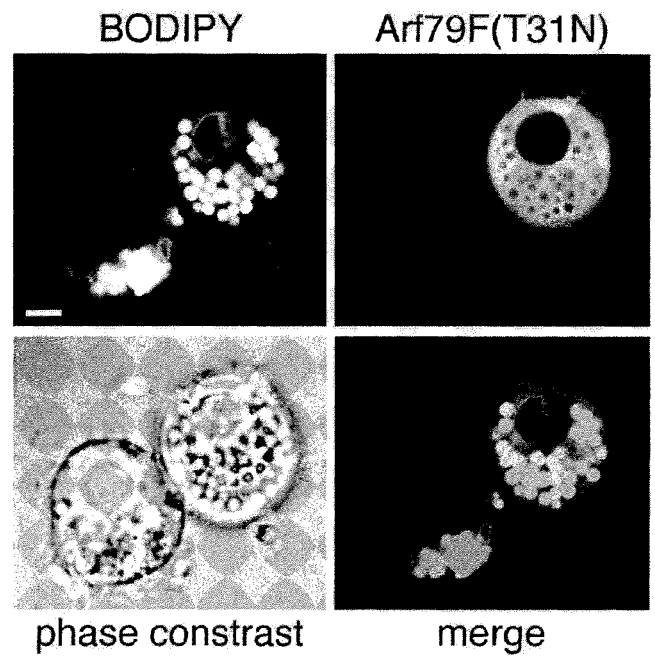
FIG. 4B is a series of micrographs showing that Arf79F (T31N) localizes to the droplet surface and causes a similar phenotype to Arf79F knockdown. Arf79F (T31N) expressed as a carboxy-terminal mCherry-tagged fusion protein in S2 cells was observed by confocal microscopy after loading with oleate and staining with BODIPY. A representative confocal midsection is shown for BODIPY (top left), mCherry fluorescence (top right) and a merge (bottom right).
Figure 4F:
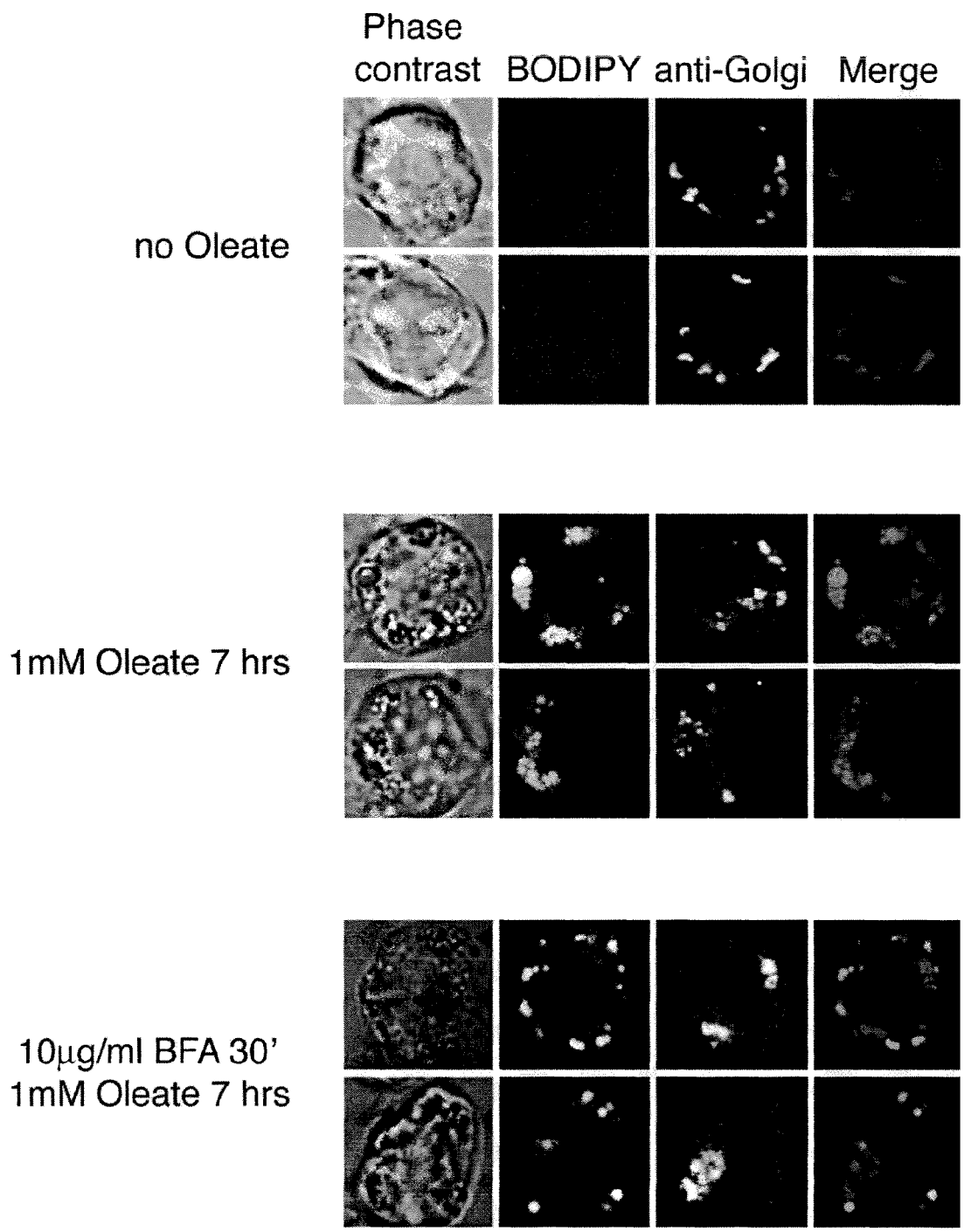
FIG. 4F shows the effects of Brefeldin A, s specific inhibitor of ARF1 exchange factors, on lipid droplet formation and dispersal.
Figure 5A:
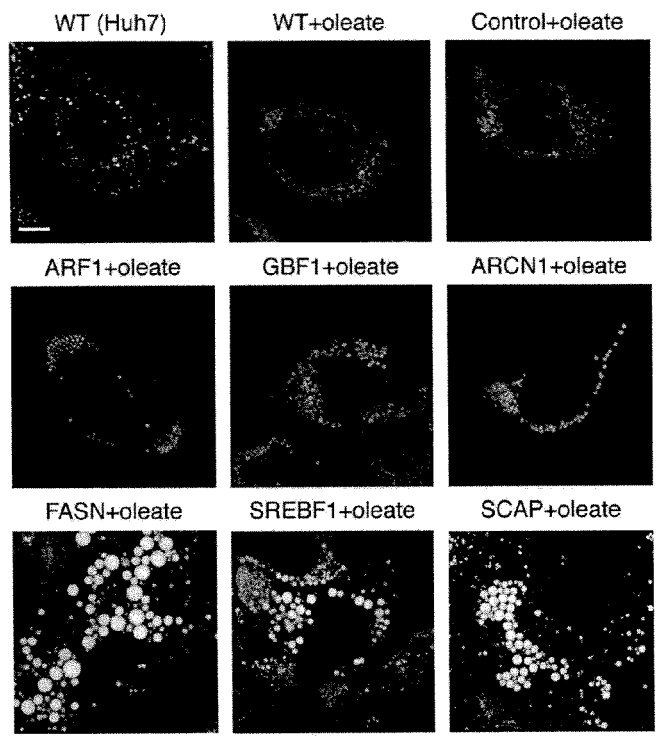
FIG. 5 is a series of photographs which shows the phenotypes of ARFI deletion in yeast and ARFI knockdown in human hepatoma (Huh7) cells and HeLa cells. (a) Huh7 cells were treated with esiRNA against ARFI (mammalian homolog of Arf79F), GBF1 (mammalian homolog of garz), ARCNI (mammalian homolog of DCop), FASN (mammalian homolog of F AS), SREBF I (mammalian homolog of SREBP), SCAP or a control esiRNA for 40 hand then incubated with 1 mM Oleate for 24 h, fixed and stained for lipid droplets with BODIPY. Representative confocal sections are shown. (b) He La cells were treated with esiRNA against control, ARFI or GBFI for 30 h and loaded with 1 mM Oleate for 24 h, stained for droplets with BODIPY and imaged on confocal microscope. The overall transfection efficiency for esiRNA was low (~10% for HuH7 cells and 50% for HeLa cells). Shown in (a) and (b) are representative images that were selected on the basis of droplet phenotypes that were similar to those observed in *Drosophila* cells and not in control knockdown cells. (c) Live yeast cells with ARFI deletion were stained with BODIPY and imaged by confocal microscopy. Controls were wild-type yeast (left) and L\4 (middle), a strain with deletions of four enzymes of neutral lipid synthesis (Dgal, Lrol, Arel, and Are2).
Figure 5B:
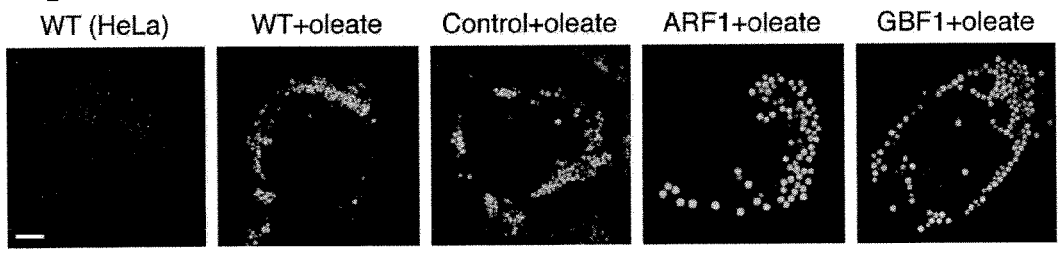
Figure 5C:
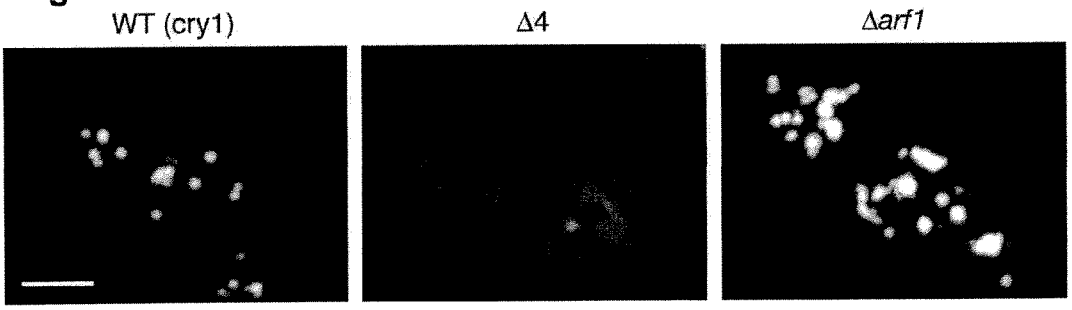

We also investigated Class III genes, whose knockdowns showed slightly larger and more dispersed droplets. Intriguingly, all Class III genes were members of the ARF1/COPI machinery, including Arf79F, an ARF1 family member, a guanine nucleoside exchange factor (GEF) garz, and components of the COPI coat. Similar effects were obtained by incubating cells with Brefeldin A, a specific inhibitor of ARF1 exchange factors (FIG. 4F), and by expressing a dominant negative version of Arf79F, the T31N mutant, analogous to dominant-negative mutants for Ras or Ran[18] (FIG. 4B). To test the specificity of this phenotype, we separately repeated RNAi knockdowns with dsRNAs for *Drosophila* genes encoding six ARF proteins, three GEFs, two GTPase-activating proteins, and all COPI subunits. We also tested other coat proteins, such as clathrin subunits and components of the COPII coat (FIG. 4A). Only Arf79f, garz, and six of eight members of the COPI coat (α, β, β', δ, γ and ζCop) exhibited the Class III phenotype, indicating that the screen conducted here identifies a highly specific subset of vesicular transport components. Arf102F knockdown gave a partial phenotype. This function of the ARF1/COPI machinery in lipid-droplet formation appears to be evolutionarily conserved; similar phenotypes were found in yeast and human cells (FIG. 5).

Figure 4C:
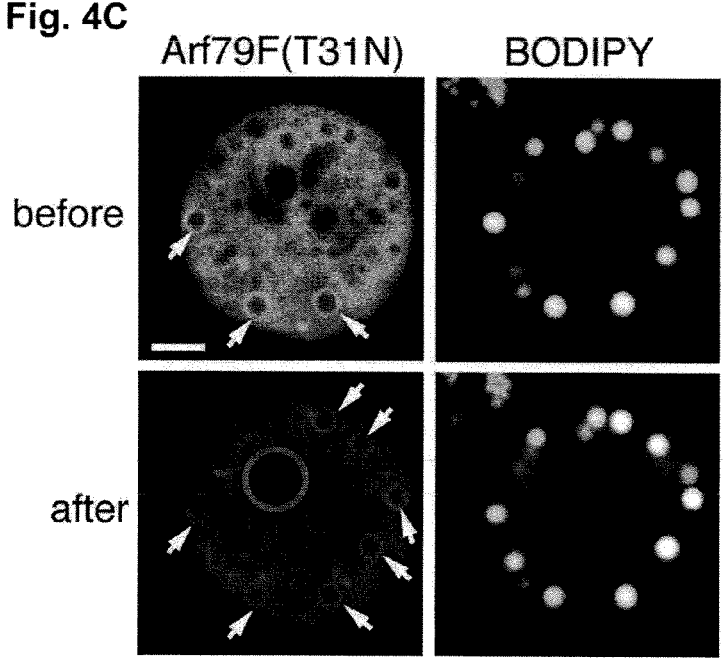
FIG. 4C is a series of micrographs showing that Arf79F (T31N)-mCherry localizes to the droplet surface. The photobleached region (6 minutes) is indicated by a circle. Arrows indicate the association of Arf79F (T31N) with the surface of droplets.

We next sought to determine if Arf79F acts directly on lipid droplets. ARF proteins exchange rapidly between active (GTP-bound) and inactive (GDP-bound) forms, making it difficult to localize only the active form. However, Arf79F (T31N) binds its exchange factor tightly, and the distribution of the exchange factor is predicted to reflect the localization of active Arf-protein. Expressed Arf79F (T31N) was present diffusely in the cytosol but was enriched at the droplet surface (FIG. 4C). Thus, Arf79F may act at the lipid-droplet surface where, as for other ARF proteins, it interacts with its GEF (presumably garz) and recruits COPI components. A recent in vitro study showed ARF1 and several subunits of the COPI complex are recruited from the cytosol to purified lipid droplets in the presence of GTP-γS[4]. Although ARF1 recruitment to lipid droplets was reported to activate phospholipase D (PLD)[19], we found no effect of PLD knockdown on lipid-droplet formation (not shown).

Figure 4D:
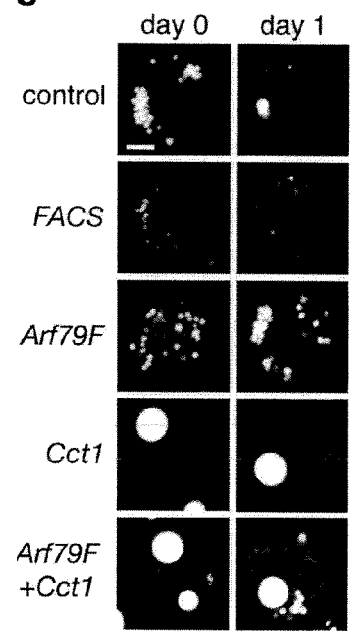
FIG. 4D is a series of micrographs showing that Arf79F, Cct1, and double knockdowns lead to decreased lipolysis. S2 cells were treated with dsRNAs for three days as indicated, loaded with 1 mM oleate for one day, and imaged by confocal microscopy after staining with BODIPY (day 0, left panels). Representative confocal midsections are shown. Oleate was removed from the medium and the cells were starved for one day in serum-free medium to induce lipolysis (day 1, right). Scale bars are 3 μm. The FACS gene encodes a long-chain-fatty-acid-CoA ligase (CG8732).
Figure 4D:
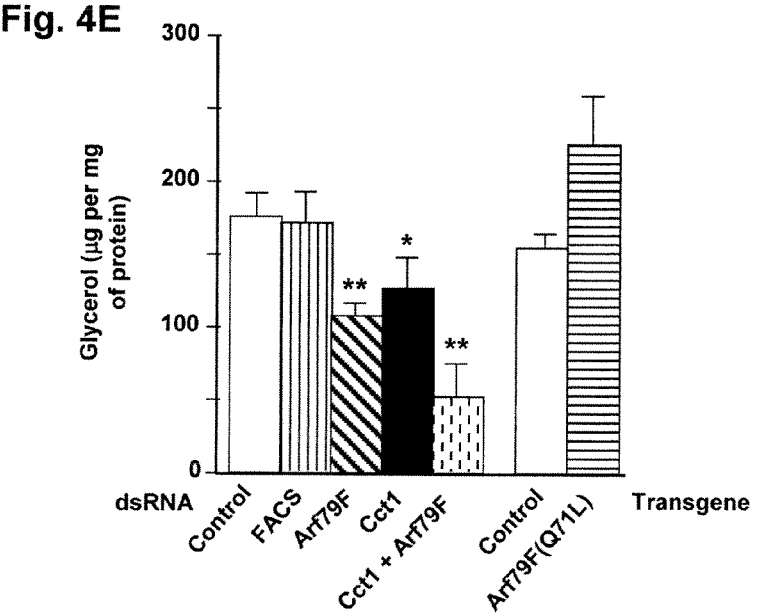

The well-established functions of Class III genes in ARF1/COPI-mediated vesicular transport[20,21] implicate this machinery in a similar budding mechanism at the surface of lipid droplets, possibly to promote budding off of droplets during lipid mobilization. Interestingly, lipolysis is associated with the break-up of larger droplets into smaller ones, presumably to provide more surface area for lipases[22]. We examined the effect of the Arf79F knockdown on lipolysis by inducing lipid-droplet formation (FIG. 4D) and then inducing lipid mobilization by incubating with serum-free medium lacking oleate. After 24 hours, control cells had few droplets. In contrast, many droplets remained when Arf79F was inactivated. Also, much less glycerol, a product of lipolysis, was released by cells lacking the ARF1/COPI machinery (FIG. 4E). Supporting a function of the ARF1/COPI machinery in lipolysis, more glycerol was released by cells expressing a dominant active form of Arf79F (Q71L). These data indicate that the ARF1/COPI machinery is required for efficient lipolysis. These data agree with a report showing that lipolysis in murine adipocytes is accompanied by a BFA-sensitive process that is required to mobilize cholesterol from storage pools in droplets[23].

Increased droplet surface area during lipolysis would require more phospholipids in the surrounding monolayer. Since Cct1 knockdown limits PC amounts, we tested its effect on lipolysis. As predicted, Cct1 knockdown dramatically decreased the efficiency of lipolysis, as seen in lipid-droplet staining (FIG. 4D) and glycerol release (FIG. 4E). The effects of knockdowns of Arf79F and Cct1 on lipolysis were additive, suggesting these genes function independently.

ARF1/COPI complexes mediate retrograde vesicular trafficking of membranes and proteins from the Golgi apparatus to the ER[21] and are also involved in vesicular transport processes from the trans-Golgi network and endosomes[21]. Notably, the members of the ARF1/COPI complex we identified were recently found in a *Drosophila* screen for genes involved in protein secretion and Golgi organization[24]. Although the primary defect in Class III knockdown cells is yet unknown, the phenotype on lipid-droplet formation is not likely an indirect consequence of inhibition of protein secretion, since i) the effects are highly specific and not observed with other proteins mediating secretory transport (ER translocation, COP II, clathrin), and ii) Arf79F is recruited to the lipid-droplet surface, as shown by us and others[4], where it is presumably activated by GTP loading on its exchange factor.

The present method employed a systematic examination of the *Drosophila* genome to identify genes involved in lipid-droplet formation and utilization. Remarkably, many genes we identified sort to distinct classes of morphological changes with each class containing functionally related proteins. These classes potentially link diverse processes, such as protein synthesis and degradation, cell cycle, and organelle movement, with lipid-droplet biology. The variety of genes identified lends support to the emerging view of lipid droplets as dynamic organelles that are functionally connected to a variety of organelles and cellular processes, including the replication of intracellular pathogens such as *Chlamydia trachomatis* and hepatitis C[25,26]. Importantly, many components of these processes are likely to be highly conserved across species. The exemplified studies in S2 cells therefore are considered to be directly relevant to cellular lipid storage in general, holding the promise of identifying pathways and mechanisms central to human diseases involving excessive lipid storage and to the engineering of cellular lipid storage in organisms for the improved production of oils and biofuels.

Given the present specific embodiments of *Drosophila* genes which, when knocked down, lower lipid content (Class I) or upregulate lipid content (Class IV), one may prepare genetically modified cells for culture or growth in plants. This will produce cells or plants which have improved biofuel properties by upregulating (class I-II) or, preferably, downregulating (class III-V) genes. Biofuels from such modified cells may be produced as described e.g., in US 20040074760 by Portnoff, et al., published Apr. 22, 2004, entitled "Production of biofuels," and U.S. Pat. No. 5,578,090 to Bradin, issued Nov. 26, 1996, entitled "Biodiesel fuel." The latter patent describes a fuel additive composition including fatty acid alkyl esters and glyceryl ethers. Similarly, a fuel additive composition can be prepared by esterifying free fatty acids and etherifying glycerol with one or more olefins in the presence of an acid catalyst, where the fatty acids were obtained using the present methods.

Lipid droplets in eukaryotic cells were long considered as inert organelles in which excess fatty acids were converted to neutral lipids to be used for metabolism, membrane synthesis (phospholipids and cholesterol), and steroid synthesis. Further evidence demonstrates that lipid droplets are complexes composed of lipids together with PAT proteins, including Perilipin (P), adipophilin (A), and tail-interacting protein of 47 kDa (TIP 47, T). Lipid droplets are a fundamental component of intracellular lipid homeostasis in all cell types, and they can provide a rapidly mobilized lipid source for many important biological processes such as membrane trafficking and cell signaling It is known that plant oils and vegetable oils are primarily made up of triple esters of glycerin and fatty acids. They are comprised of triglycerides, as are the lipid droplets studies in the present examples. Methods for transforming plants are known. For example, US 2007/0214516 to Fillatti, et al., published Sep. 13, 2007, entitled "Soybean Seed and Oil Compositions and Methods of Making Same," discloses methods and vectors for transforming soybean. In addition, the present genes may be searched to obtain appropriate orthologs in the plant cells to be modified. It is not necessary to obtain orthologs, however, as plants are know to be able to express functional genes from other organisms. For example, the cct1 gene is known to have counterparts in *Arabidopsis thaliana*, as indicated by NCBI Homologene search. Homologous genes may be expected to exist in other plants, such as corn or soybean. The soybean genome is known, see soybeangenome.siu.edu/. By using the BLAST tool provided, one obtains a number of significantly similar genes, such as X86970, 1950 bp mRNA G.soja mRNA for glycinin ACCESSION X86970. One may then knockout the corresponding gene to *Drosophila* cct1 in soya and observe resultant cells and plants for increased presence of lipid droplets. In addition, one may upregulate lipid production in plant cells by using the *Drosophila* genes themselves, since lipid regulation is conserved across species lines. As described below, double knockdowns of Arf79F and Cct1 were created. Droplets were more numerous in the ARF1 deletion. Further, counterparts are known to exist in other species. CCT1 is shown here to act in a different manner, and to result in a phenotype of fewer, larger lipid droplets. It is shown here that a Cct1 knockdown has in creased cellular triglycerides in S2 cells. Cct1 knockdowns also have impaired droplet mobilization. Thus, one may use either or both of these genes, or their orthologs in a method of increasing lipid production in a cell comprising the step of decreasing expression of a gene in that cell that is most closely identical in sequence to Arf79F and/or a gene in that cell that is most closely identical in sequence to Cct1. It is shown here also that garz and COPI are in the same phenotypic class as ARf79F and can be utilized in the same way. SREBP, SCAP, and FAS are similar to CCT1 and may be used in the same way.

EXAMPLES

Example 1

Methods Summary

Chemicals and materials. Oleic acid (Sigma-Aldrich) and 10% BSA (essentially fatty acid free, Sigma-Aldrich) were used to make a 7.5 mM stock solution (5:1 oleic acid:BSA molar ratio)[31]. BODIPY 493/503 was from Invitrogen.

Cell culture. *Drosophila* S2 cells were cultured in Schneider's *Drosophila* medium (Invitrogen) supplemented with 10% fetal bovine serum and antibiotics (100 unit/ml penicillin and 100 μg/ml streptomycin) at 25° C. as described[32]. RNAi treatment of S2 cells were performed as previously described[10]. A segment of pBluescript backbone was used as the template for control RNAi (referred as control RNAi thereafter). Transfection of S2 cells was performed using Cellfectin reagent (Invitrogen). Images of live cells were taken using LSM 510 confocal microscope (Carl Zeiss MicroImaging) with a 63× oil immersion lens.

RNAi-mediated genomic screen. RNAi screening with UCSF DmRNAi libraries versions 1 and 2 (15,683 genes) was as described[10]. The primary visual screen was validated by treating S2 cells with an independent set of RNAs[8-10].

Figure 2C:
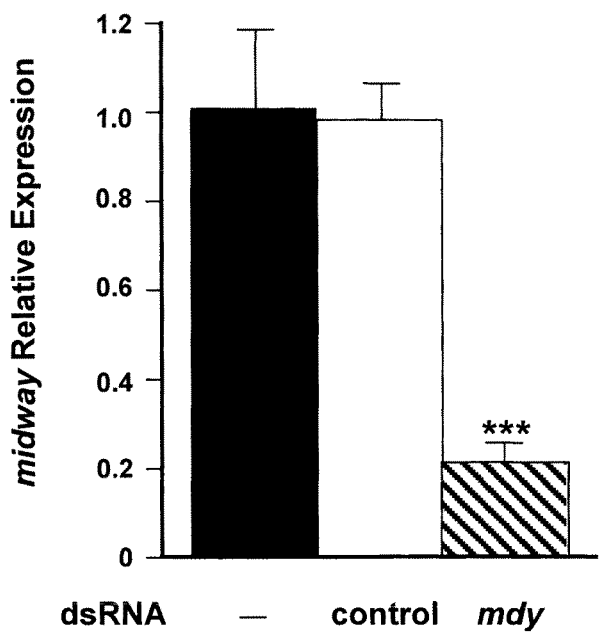
FIG. 2C shows the results of knock-down of mdy and Arf79F genes by RNAi treatment.
Figure 2D:
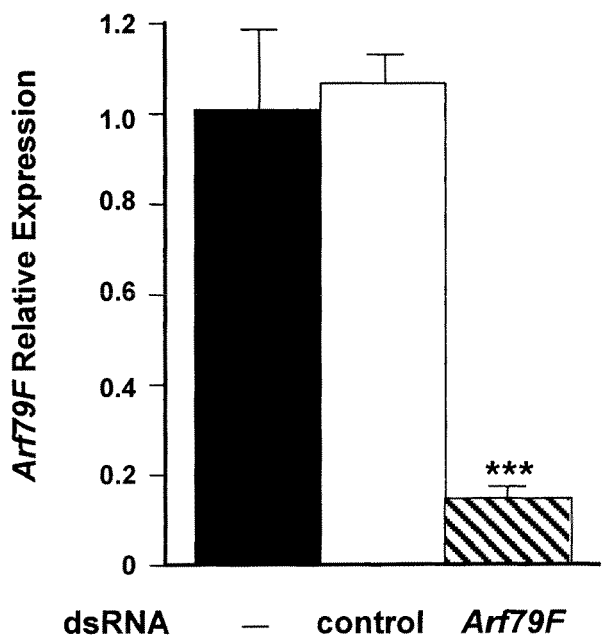
FIG. 2 shows a gene identification strategy and phenotypic classes found when a genome-wide screen was conducted to identify genes regulating the formation of lipid droplets.

PCR analysis of RNAi knockdowns. Primers used for the original screen can be found at rnai.ucsf.edu and for secondary validation can be found at mpibcms.biochem.mpg.de/en/rg/lipidrophe/absatz_01.html. Examination of selected genes by real-time PCR demonstrated 80-90% mRNA knockdown (FIG. 2C); previous studies showed proteins reduced by 80%[27,28]. For all gene knockdowns, the penetrance of the phenotypes was high, affecting more than 70-80% of the cells.

Electron microscopy. RNAi treated cells were cultured with 1 mM oleate incubation for 24 hours, fixed in 1.5% glutaraldehyde, 4% polyvinylpyrrolidone, 0.05% calcium chloride, 0.1 M sodium cacodylate, pH 7.4, on ice, and then pelleted. The samples were stained for lipid using an imidazole-buffered osmium tetroxide method[33], then block-stained in 2% uranyl acetate overnight at 4° C., dehydrated, infiltrated and embedded in LX-112 resin (Ladd Research Industries). Samples were sectioned ultrathin (65 nm) on a Reichert Ultracut S ultramicrotome and stained with 0.8% lead citrate. Grids were examined on a JEOL JEM-1230 electron microscope (JEOL, USA Inc.) and photographed using the Gatan Ultrascan 1000 digital camera (Gatan, Inc.).

Image analyses. S2 cells ($2.7 \times 10^6$ cells/ml) were treated with 1 μg dsRNA in 96-well plates for 3 days, and 1 mM oleic acid was added for 24 h. Cells were fixed in 4% paraformaldehyde/PBS (1 h) and stained with DAPI and BODIPY493/503 in PBS (1 h). Images were obtained with IC100 (Beckman) or ImageXpress Micro (Molecular Devices) automated microscopes and a 40×, 0.95 NA PlanApo dry objective lens (Nikon). Six image fields (400-600 cells/well) were acquired per RNAi. For all gene knockdowns, the penetrance of the phenotypes was high, affecting more than 70-80% of the cells.

Visual image analyses of the RNAi screen. Both the first (15,683 genes; whole genome) and second (847 repeated genes) data sets were scored visually by the same two independent observers who were blinded to gene identities. In total, nearly 95,000 images (15,643 genes, with 6 images per gene), each with several hundred cells, were examined visually. For visual scoring, a MAT LAB script was utilized that allowed lipid droplets in each image (six per gene) to be scored for three criteria: number (more, normal, fewer), size (smaller, normal, larger), and dispersion (more, normal, less). These scores were imported to a spreadsheet to compile a hit list. In the first round of visual scoring, hits were defined as those genes identified as abnormal by both observers. The same observers and procedures were used in the visual screen of the repeat data setscreen of the repeat data set.

Automated image analyses. Both the initial and repeat data sets were analyzed by automated image analysis. OAPI and BODIPY images from the initial screen were analyzed by using a series of MAT LAB scripts. In short, OAPI images were used to segment the images into individual cells by using Otsu's thresholding 34 and watershed segmentation from the image processing toolbox. Similarly, the BODIPY signal outline was determined by thresholding.

The cell shapes were overlaid on the BODIPY image and several parameters of the BOOIPY signal (e.g., size, intensity, and numbers of clusters) were measured and averaged per cell, excluding cells at the boundary of the image and cell clumps. Images with few cells were flagged, as were images with abnormal OAPI signals. Among the parameters, the total signal per image, and the number of clusters and the mean signal per cell proved most useful and were further used for statistical analysis. In particular, for descriptive statistics, the interquartile range (IQR) was determined for the values of each parameter and conditions that resulted in a signal more than 1.5 deviant from the lower (0.25) or higher (0.75) percentile were considered hits for this category. Lists of hits for each category were compiled in a spreadsheet and compared with the results from visual screening.

Computational analysis using quantitative PCR. dsRNAs (16 μg) were added to individual wells of 6-well plates. After 4 days, cells were harvested and lysed in RNA-Stat-60 (Tel-test). Total RNA (1.5 μg) was used to synthesize first strand cDNAs by using SuperscriptIII reverse transcriptase and random hexomer primers (Invitrogen).

Real-time quantitative PCR was performed with the AB1 Perkin Elmer Prism 7700 (Applied Biosystems) and SYBR green detection of amplified products. Each 25 μl PCR reaction mix contained 2 μl cDNA, 12.5 μl 2× SYBR Green master mixture (Qiagen) and 600 nM of primers (midway forward: 5'-CCAAGCTGGTGCAATATCCT-3' (SEQ ID NO:1), midway reverse: 5'-CACCACCTC-CAATAAACGCT-3' (SEQ ID NO:2), Arj79F forward: 5'-GTCGCCTGGATGT ACCAGTT-3' (SEQ ID NO:3), Arj79F reverse: 5'-GTATCGGTGAGGCGAGAGAG-3', (SEQ ID NO:4) Aldh forward: 5'-GAGGGCCTACCCGGC-TACT-3' (SEQ ID NO:5), and Aldh reverse: 5'-CTCCCTTG-CAA TGGTCA TA TCA-3' (SEQ ID NO:6). Aldh (Aldehyde dehydrogenase) 35 was used as an internal reference gene.

Protein localization. mCherry was from Roger Tsien[7]. mCherry-CCT1, mCherry-CCT2, and Arf79F-mCherry expression vectors (actin promoter) were made with the Gateway system (Invitrogen). Arf79F (T31N)-mCherry and Arf79F (Q71L)-mCherry were generated by QuickChange II mutagenesis (Stratagene).

Lipid measurements. Cells were cultured in 6-well plates (16 μg dsRNAs each well) for 3 days, and then 1 mM oleate was added for 24 hours. Cells were lysed in 50 mM Tris-HCl (pH 7.4), 0.25 M sucrose, and samples (250 μg protein) were assayed for lipids. PC was quantified with a colorimetric method[29]. TG content was measured from extracted lipids by TLC[30].

Lipolysis studies. Cells were cultured with 1 mM oleate for 24 h. To stimulate lipolysis, oleate was removed, and cells were cultured in serum-free media for 24 h. Aliquots were analyzed for glycerol (Sigma-Aldrich) and protein (Bio-Rad $D_C$ Protein Assay) content.

*Saccaromyces cerevisiae* studies. Strains examined were wild-type (Cry1, W303), a control strain (Δ4) lacking neutral lipid synthesis enzymes (Dgal, Lrol, Arel, Are2) and lipid droplets, and Δarfl (W303). Yeast strains were cultured in YPD media. At O.D.600=0.8, aliquots were taken from culture and BODIPY (1 μg/ml) dye was added. Images were obtained with a LSM 510 confocal microscope (Carl Zeiss MicroImaging). The results of this study are shown in FIG. 5.

Endoribonuclease-prepared short-interfering RNA (esiRNA) treatment of hepatoma cells and HeLa cells. esiRNAs targeting ARFI (mammalian homolog of Arj79F), GBF1 (mammalian homolog of garz), ARCNI (mammalian homolog of δCop), FASN (mammalian homolog of FAS), SREBF1 (mammalian homolog of SREBP) and SCAP were generated with published methods[36,37]. The endonuclease RNaseIII was a gift from Barbara Panning. Purified esiRNAs (20 ng) were transfected with Lipofectamine (Invitrogen) into Huh7 human hepatoma cell line in 24-well plates. After culture for 40 h in DMEM medium, 1 mM oleate was added to the medium and cells were incubated for another 24 h. Cells were then stained with BODIPY and imaged with LSM 510 confocal microscope (Carl Zeiss MicroImaging). A similar protocol was used for HeLa cell RNAi treatment with the exception of transfection with DharmFECT (Dharmacon) for 30 h before loading with 1 mM Oleate. The results of this study are shown in FIG. 5.

Example 2

Methods of modulating lipid concentration in a eukaryotic cell

The present invention provides methods of modulating lipid concentration in a eukaryotic cell by increasing or decreasing expression of a gene, or an ortholog of a gene, selected from the genes listed above in Table 1, Table 2 or Table 3. In one embodiment, lipid concentration is increased, either by decreasing the expression of a gene found in phenotypic classes III, IV, or V, or by increasing expression of a gene found in phenotypic classes I or II. In another embodiment, lipid concentration is decreased, either by increasing expression of a gene found in phenotypic classes III, IV, or V, or by decreasing expression of a gene found in phenotypic classes I or II.

Finding Orthologs of Genes Listed in Tables 1, 2, or 3

Orthologs of the genes listed in Tables 1, 2, and 3 may be found using any method known in the art. In one example, a BLAST or other computer search is used to identify orthologs in various species. This technique is especially useful when looking for orthologs in a species whose genome has been sequenced. In another example, PCR primers based on the sequence of the *Drosophila* genes are used to amplify genetic material in the species of interest.

Methods of Decreasing Expression of a Gene Listed in Table 1, 2, or 3

Gene expression may be decreased using any method known in the art. In a preferred embodiment, a vehicle that provides an inhibitory, double stranded inhibitory, or antisense RNA is used to specifically decrease expression of the desired gene. See, for example, US Patent Publication No. 2007/0025969, by Roelvink et al, titled "RNAi expression constructs"; US Patent Publication No. 2006/0174380, Carrington et al, titled "Method to trigger RNA interference"; and U.S. Pat. No. 5,908,779, issued to Carmichael et al, titled "Targeted RNA degradation using nuclear antisense RNA," all of which are incorporated by reference in their entirety. Other techniques may also be used, e.g., use of ribozymes, promoter silencing, and DNA binding proteins.

Method of Increasing Expression of a Gene Listed in Table 1, 2, or 3

Gene expression may be increased using any method known in the art. In a preferred embodiment, the desired gene is transfected into the eukaryotic cell by incorporating it into a construct, such as a plasmid or viral construct. Design of such a construct is within the skill of the art (See, e.g., Plant Molecular Biology: A laboratory Manual, Clark (ed.), Springer, N.Y. (1997) and Molecular Cloning, A Laboratory Manual, Sambrook et al. eds. Cold Spring Harbor Press: New York (1989)). The construct may then be introduced into the cell using, for example, liposomes, viral vectors, electroporation, etc. See, for example, U.S. Pat. No. 5,279,833, issued to Rose, titled "Liposomal transfection of nucleic acids into animal cells"; U.S. Pat. No. 5,928,944, issued to Seth et al., titled "Method of adenoviral-mediated cell transfection; U.S. Pat. No. 5,389,069, issued to Weaver, titled "Method and apparatus for in vivo electroporation of remote cells and tissue"; and US Patent Application Publication No. 2005/0034190, Filatti et al., titled "Nucleic acid constructs and methods for producing altered seed oil compositions," all of which are incorporated by reference herein in their entirety.

Methods of Extracting Lipids From a Eukaryotic Cell and Using Said Cells as a Source of Biofuel Lipids can be extracted using any method known in the art. See, e.g., U.S. Pat. No. 5,516,923, issued to Hebert et al, titled "Extracting oil from oil-bearing plant parts". In addition, the cells of the present invention may be used as a source of biodiesel fuel. See, e.g., US Patent Application No. 2007/0048848, by Sears, titled "Method, apparatus, and system for biodiesel production from algae"; and U.S. Pat. No. 6,015,440, issued to Noureddini, titled "Process for producing biodiesel fuel with reduced viscosity and cloud point below 32 degrees Fahrenheit," both of which are incorporated by reference herein in their entirety.

Example 3

Method of Identifying Disease Markers

The present invention also provides a method of identifying a diagnostic marker of a disease characterized by an excess of lipids, comprising comparing the level of expression of a gene selected from the genes listed in Table 1, 2, or 3, or an ortholog thereof, in organisms with and without said disease; determining if there is a difference in the level of expression of said gene in organisms with and without said disease; and identifying said gene as a diagnostic marker based on said determining. Gene expression may be compared using any method known in the art. In a preferred embodiment, a microarray is used to simultaneously compare expression of a large number of genes. Differences may be confirmed, for example using Northern blots, Western blots, immunocytochemistry, quantitative PCR, etc.

For example, the *Drosophila* gene cct1, shown here to modulate lipid drop formation, has a human ortholog, as identified in Flybase.net. This is the peptide PCYT1A-201. This is also a choline phosphate cytidylyltransferase, and based on the present findings can be used as a disease marker in humans.

CONCLUSION

The above specific description is meant to exemplify and illustrate the invention and should not be seen as limiting the scope of the invention, which is defined by the literal and equivalent scope of the appended claims. Any patents or publications mentioned in this specification are indicative of levels of those skilled in the art to which the patent or publication pertains as of its date and are intended to convey details of the invention which may not be explicitly set out but which would be understood by workers in the field. Such patents or publications are hereby incorporated by reference to the same extent as if each was specifically and individually incorporated by reference, such incorporation being for the purpose of further describing and enabling the method or material referred to.

REFERENCES

1. Bartz, R. et al. Lipidomics reveals that adiposomes store ether lipids and mediate phospholipid traffic. *J Lipid Res* 48, 837-47 (2007).
2. Brown, D. A. Lipid droplets: proteins floating on a pool of fat. *Curr Biol* 11, R446-9 (2001).
3. Miura, S. et al. Functional conservation for lipid storage droplet association among Perilipin, ADRP, and TIP47 (PAT)-related proteins in mammals, *Drosophila*, and *Dictyostelium*. *J Biol Chem.* 277, 32253-7 (2002).
4. Bartz, R. et al. Dynamic activity of lipid droplets: protein phosphorylation and GTP-Mediated protein translocation. *J Proteome Res* 6, 3256-65 (2007).
5. Martin, S. & Parton, R. G. Lipid droplets: a unified view of a dynamic organelle. *Nat Rev Mol Cell Biol* 7, 373-8 (2006).
6. Ulvila, J. et al. Double-stranded RNA is internalized by scavenger receptor-mediated endocytosis in *Drosophila* S2 cells. *J Biol Chem* 281, 14370-5 (2006).
7. Shaner, N. C. et al. Improved monomeric red, orange and yellow fluorescent proteins derived from *Discosoma* sp. red fluorescent protein. *Nat Biotechnol* 22, 1567-72 (2004).
8. Ma, Y., Creanga, A., Lum, L. & Beachy, P. A. Prevalence of off-target effects in *Drosophila* RNA interference screens. *Nature* 443, 359-63 (2006).
9. Kulkarni, M. M. et al. Evidence of off-target effects associated with long dsRNAs in *Drosophila melanogaster* cell-based assays. *Nat Methods* 3, 833-8 (2006).
10. Goshima, G. et al. Genes required for mitotic spindle assembly in *Drosophila* S2 cells. *Science* 316, 417-21 (2007).
11. Brown, M. S. & Goldstein, J. L. A proteolytic pathway that controls the cholesterol content of membranes, cells, and blood. *Proc. Natl. Acad. Sci. USA* 96, 11041-11048 (1999).
12. Dobrosotskaya, I. Y., Seegmiller, A. C., Brown, M. S., Goldstein, J. L. & Rawson, R. B. Regulation of SREBP processing and membrane lipid production by phospholipids in *Drosophila*. *Science* 296, 879-83 (2002).
13. Kent, C. Regulatory enzymes of phosphatidylcholine biosynthesis: a personal perspective. *Biochim Biophys Acta* 1733, 53-66 (2005).
14. Morrison, D. K., Murakami, M. S. & Cleghon, V. Protein kinases and phosphatases in the *Drosophila* genome. *J Cell Biol* 150, 57-62 (2000).
15. Cornell, R. B. & Northwood, I. C. Regulation of CTP: phosphocholine cytidylyltransferase by amphitropism and relocalization. *Trends Biochem Sci* 25, 441-7 (2000).
16. Weber, U., Eroglu, C. & Mlodzik, M. Phospholipid membrane composition affects EGF receptor and Notch signaling through effects on endocytosis during *Drosophila* development. *Dev Cell* 5, 559-70 (2003).
17. Hafez, I. M. & Cullis, P. R. Roles of lipid polymorphism in intracellular delivery. *Adv Drug Deliv Rev* 47, 139-48 (2001).
18. Dascher, C. & Balch, W. E. Dominant inhibitory mutants of ARF1 block endoplasmic reticulum to Golgi transport and trigger disassembly of the Golgi apparatus. *J Biol Chem* 269, 1437-48 (1994).
19. Nakamura, N., Banno, Y. & Tamiya-Koizumi, K. Arf1-dependent PLD1 is localized to oleic acid-induced lipid droplets in NIH3T3 cells. *Biochem Biophys Res Commun* 335, 117-23 (2005).
20. Spang, A., Matsuoka, K., Hamamoto, S., Schekman, R. & Orci, L. Coatomer, Arf1p, and nucleotide are required to bud coat protein complex I-coated vesicles from large synthetic liposomes. *Proc Natl Acad Sci USA* 95, 11199-204 (1998).
21. D'Souza-Schorey, C. & Chavrier, P. ARF proteins: roles in membrane traffic and beyond. *Nat Rev Mol Cell Biol* 7, 347-58 (2006).
22. Marcinkiewicz, A., Gauthier, D., Garcia, A. & Brasaemle, D. L. The phosphorylation of serine 492 of perilipin a directs lipid droplet fragmentation and dispersion. *J Biol Chem* 281, 11901-9 (2006).
23. Verghese, P. B., Arrese, E. L. & Soulages, J. L. Stimulation of lipolysis enhances the rate of cholesterol efflux to HDL in adipocytes. *Mol Cell Biochem* 302, 241-8 (2007).
24. Bard, F. et al. Functional genomics reveals genes involved in protein secretion and Golgi organization. *Nature* 439, 604-7 (2006).
25. Kumar, Y., Cocchiaro, J. & Valdivia, R. H. The obligate intracellular pathogen Chlamydia trachomatis targets host lipid droplets. *Curr Biol* 16, 1646-1651 (2006).
26. Miyanari, Y. et al. The lipid droplet is an important organelle for hepatitis C virus production. *Nat Cell Biol* 9, 1089-97 (2007).
27. Goshima, G. & Vale, R. D. The roles of microtubule-based motor proteins in mitosis: comprehensive RNAi analysis in the *Drosophila* S2 cell line. *J Cell Biol* 162, 1003-16 (2003).
28. Rogers, S. L., Wiedemann, U., Stuurman, N. & Vale, R. D. Molecular requirements for actin-based lamella formation in *Drosophila* S2 cells. *J Cell Biol* 162, 1079-88 (2003).
29. Hojjati, M. R. & Jiang, X. C. Rapid, specific, and sensitive measurements of plasma sphingomyelin and phosphatidylcholine. *J Lipid Res* 47, 673-6 (2006).
30. Monetti, M. et al. Dissociation of hepatic steatosis and insulin resistance in mice overexpressing DGAT in the liver. *Cell Metab* 6, 69-78 (2007).
31. Stone, S. J. et al. Lipopenia and skin barrier abnormalities in DGAT2-deficient mice. *J Biol Chem* 279, 11767-76 (2004).
32. Clemens, J. C. et al. Use of double-stranded RNA interference in *Drosophila* eel lines to dissect signal transduction pathway. *Proc Natl Acad Sci USA* 97, 6499-503 (2000).
33. Angermüller, S. & Fahimi, H. D. Imidazole-buffered osmium tetroxide: An excellent stain for visualization of lipids in transmission electron microscopy. *Histochem.* 1. 14,823-835 (1982).
34. Otsu, N. A threshold selection method from gray-level histrograms. *IEEE Trans Syst Man Cybern* 9,62-66 (1979).
35. Seegmiller, A. C. et al. The SREBP pathway in *Drosophila*: regulation by palmitate, not sterols. *Dev Cell* 2, 229-38 (2002).
36. Yang, D. et al. Short RNA duplexes produced by hydrolysis with *Escherichia coli* RNase III mediate effective RNA interference in mammalian cells. *Proc Natl Acad Sci USA* 99, 9942-7 (2002).
37. Kittler, R., Heninger, A. K., Franke, K., Habermann, B. & Buchholz, F. Production of endoribonuclease-prepared short interfering RNAs for gene silencing in mammalian cells. *Nat Methods* 2, 779-84 (2005).
38. Cermelli, S., Guo, Y, Gross, S. P., Welte, M. A. The lipid-droplet proteome reveals that droplets are a protein-storage depot. *Curr Biol.* 16, 1783-95 (2006).

What is claimed is:

1. A method of increasing lipid production in a eukaryotic cell, comprising genetically altering said cell for altered expression level of a gene whose alteration has a visible phenotypic effect on either or both of (a) lipid droplet size or (b) lipid droplet number in cells in said cell culture and extracting lipids from said eukaryotic cell, wherein said gene is selected from the group consisting of arf-COPI genes, garz, and orthologs thereof.

2. The method of claim 1 where the cells in the cell culture exhibit reduced lipid concentration by increasing expression of said gene, or increased lipid concentration in said cell by reducing expression of said gene, where reducing gene expression results in larger, dispersed lipid droplets, and said gene is selected from the group consisting of arf-COPI genes and garz.

3. The method of claim 1, further comprising transfecting said eukaryotic cell with said gene.

4. The method of claim 1, wherein said eukaryotic cell is a plant, fungal or animal cell.

5. The method as set forth in claim 4, wherein said eukaryotic cell is a plant cell, and wherein said plant is selected from the group consisting of soy, coconut, corn, cotton, flax, palm, rapeseed, canola, safflower, sunflower, and algae.

6. The method of claim 1, wherein said eukaryotic cell is a yeast cell.

7. The method of claim 1, further comprising the step of producing a biofuel after said extracting of lipid droplets.

8. The method of claim 1 wherein said gene is an Arf gene and said altered expression is lowered expression.

9. The method of claim 1 wherein said gene is Arf or COPI and further comprising the step of lowering gene expression in said eukaryotic cell by RNAi.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: artificial
<220> FEATURE:
<223> OTHER INFORMATION: PCR primer

<400> SEQUENCE: 1
ccaagctggt gcaatatcct                                               20

<210> SEQ ID NO 2
<211> LENGTH: 20
<212> TYPE: DNA
<213> ORGANISM: artificial
<220> FEATURE:
<223> OTHER INFORMATION: PCR primer

<400> SEQUENCE: 2
caccacctcc aataaacgct                                               20

<210> SEQ ID NO 3
<211> LENGTH: 20
<212> TYPE: DNA
<213> ORGANISM: artificial
<220> FEATURE:
<223> OTHER INFORMATION: PCR primer

<400> SEQUENCE: 3
gtcgcctgga tgtaccagtt                                               20

<210> SEQ ID NO 4
<211> LENGTH: 20
<212> TYPE: DNA
<213> ORGANISM: artificial
<220> FEATURE:
<223> OTHER INFORMATION: PCR primer

<400> SEQUENCE: 4
gtatcggtga ggcgagagag                                               20

<210> SEQ ID NO 5
<211> LENGTH: 19
<212> TYPE: DNA
<213> ORGANISM: artificial
<220> FEATURE:
<223> OTHER INFORMATION: PCR primer

<400> SEQUENCE: 5
gagggcctac ccggctact                                                19

<210> SEQ ID NO 6
<211> LENGTH: 22
<212> TYPE: DNA
<213> ORGANISM: artificial
<220> FEATURE:
<223> OTHER INFORMATION: PCR primer

<400> SEQUENCE: 6
ctcccttgca atggtcatat ca                                            22